(12) United States Patent
Riu et al.

(10) Patent No.: US 11,326,181 B2
(45) Date of Patent: May 10, 2022

(54) METHOD FOR PRODUCING TRANSGENIC PLANT HAVING INCREASED CONTENT OF 20-HYDROXYECDYSONE USING INSECT-DERIVED GENE AND PLANT PRODUCED BY THE SAME

(71) Applicant: WOOJUNG BIO INC., Gyeonggi-do (KR)

(72) Inventors: Key Zung Riu, Jeju-do (KR); Kyung Hwan Boo, Jeju-do (KR); Byung Nyun Chun, Gyeonggi-do (KR); Jung Kyu Suh, Gyeonggi-do (KR); Jiwon Kim, Jeju-do (KR)

(73) Assignee: WOOJUNG BIO INC., Gyeonggi-Do (KR)

( * ) Notice: Subject to any disclaimer, the term of this patent is extended or adjusted under 35 U.S.C. 154(b) by 0 days.

(21) Appl. No.: 16/759,605

(22) PCT Filed: Nov. 1, 2018

(86) PCT No.: PCT/KR2018/013177
§ 371 (c)(1),
(2) Date: Apr. 27, 2020

(87) PCT Pub. No.: WO2019/088730
PCT Pub. Date: May 9, 2019

(65) Prior Publication Data
US 2020/0299720 A1 Sep. 24, 2020

(30) Foreign Application Priority Data
Nov. 2, 2017 (KR) .................. 10-2017-0145435

(51) Int. Cl.
*C12N 15/82* (2006.01)
(52) U.S. Cl.
CPC ..... *C12N 15/8286* (2013.01); *C12N 15/8243* (2013.01)
(58) Field of Classification Search
None
See application file for complete search history.

(56) References Cited

U.S. PATENT DOCUMENTS

| | | | |
|---|---|---|---|
| 4,940,838 A | 7/1990 | Schilperoort et al. | |
| 10,351,875 B2 * | 7/2019 | Riu | C12N 15/8286 |

FOREIGN PATENT DOCUMENTS

| | | | |
|---|---|---|---|
| EP | 0 116 718 B1 | 5/1990 | |
| EP | 0 120 516 B1 | 10/1991 | |
| EP | 0 301 316 B1 | 6/1993 | |
| KR | 10-2015-0061840 A | 6/2015 | |
| WO | WO 2015/080494 | * 6/2015 | |

OTHER PUBLICATIONS

C2 hydroxylase in UniProtKB, ttps://www.uniprot.org/uniprot/?query=c2+hydroxylase+AND+reviewed%3Ayes&sort=score, Accessed May 28, 2021.*
C14 hydroxylase in UniProtKB, https://www.uniprot.org/uniprot/?query=c14%20hydroxylase&fil=reviewed%3Ayes&sort=score, Accessed May 28, 2021.*
C22 hydroxylase in UniProtKB, https://www.uniprot.org/uniprot/?query=c22+hydroxylase+AND+reviewed%3Ayes&sort=score, Accessed May 28, 2021.*
C20 hydroxylase in UniProtKB, https://www.uniprot.org/uniprot/?query=c20+hydroxylase+AND+reviewed%3Ayes&sort=score, Accessed May 28, 2021.*
C25 hydroxylase in UniProtKB, https://www.uniprot.org/uniprot/?query=c25+hydroxylase+AND+reviewed%3Ayes&sort=score, Accessed May 28, 2021.*
Short-chain _dehydrogenase reductase_ in UniProtKB, https://www.uniprot.org/uniprot/?query=short-chain%20%22dehydrogenase%20reductase%22&fil=reviewed%3Ayes&sort=score, Accessed May 28, 2021.*
Persson et al, 2009, Chem. Biol. Interact. 178: 94-98; author manuscript provided.*
Muramatsu et al, 2020, PLoS ONE 15 (4): e0231451. https://doi.org/10.1371/journal.pone.0231451.*
Niwa et al, 2014, Biosci. Biotech. Biochem. 78:1283-1292.*
Dermauw et al, 2020, Insect. Biochem. Mol. Biol. 127:103490.*
FlyBase Gene Report Dmel/Cyp6T3, http://flybase.org/reports/FBgn0033697.html, accessed Jun. 7, 2021.*
Wang et al, 2017, Front. Plant Sci. 8:266.*
UniProtKB/Swiss-Prot: Q9VWR5, 2021, https://www.ncbi.nlm.nih.gov/protein/Q9VWR5.*
UniProtKB/Swiss-Prot: Q9VGH1, 2021, https://www.ncbi.nlm.nih.gov/protein/Q9VGH1.*
Miwa R. et al., "Non-molting glossy/shroud encodes a short-chain dehydrogenase/reductase that functions in the 'Black Box' of the ecdysteroid biosynthesis pathway", Development, vol. 137(12), pp. 1991-1999.
NCBI Reference Sequence: NM_001177862.1: Bombyx Mori Short-chain Dehydrogenase/reductase (SDR1), mRNA, Jun. 25, 2017.
NCBI Reference Sequence: NM_001111363.1: Bombyx mori cytochrome P450 (Cyp307a1), mRNA, Jun. 10, 2017.
NCBI Reference Sequence: NM_001112751.2: Bombyx mori cytochrome P450 monooxygenase (Cyp306a1), mRNA, Jun. 12, 2017.

(Continued)

Primary Examiner — Anne Kubelik
(74) Attorney, Agent, or Firm — The PL Law Group, PLLC

(57) ABSTRACT

A method for producing a transgenic plant having increased content of 20-hydroxyecdysone according to an embodiment of the present invention may use insect-derived gene A method according to an embodiment of the present invention includes transforming a plant cell with a recombinant vector including at least one of a gene encoding short-chain dehydrogenase/reductase (SDR) protein and a gene encoding C-14 hydroxylase protein, a gene encoding C-25 hydroxylase protein, a gene encoding C-22 hydroxylase protein, a gene encoding C-2 hydroxylase protein, and a gene encoding C-20 hydroxylase protein derived from insect, and regenerating a plant from the transformed plant cell.

14 Claims, 12 Drawing Sheets

Specification includes a Sequence Listing.

(56) References Cited

OTHER PUBLICATIONS

NCBI Reference Sequence: NM_001043488.1, Bombyx mori cytochrome P450 302A1 (Cyp302a1), mRNA, Jun. 25, 2017.
NCBI Reference Sequence: NM_001112753.1: Bombyx Mori Cytochrome P450 (Cyp315a1), mRNA, Jun. 25, 2017.
NCBI Reference Sequence: NM_001112748.1, Bombyx mori ecdysone 20-hydroxylase (Cyp314a1), mRNA, Jun. 25, 2017.
Krens, F.A. et al., "In vitro transformation of plant protoplasts with Ti-plasmid DNA", Nature vol. 296, pp. 72-74, 1982.
Negrutiu I. et al., "Hybrid genes in the analysis of transformation conditions I. Setting up a simple method for direct gene transfer in plant protoplasts", Plant Mol. Biol. 8, pp. 363-373, 1987.
Crossway A. et al., "Integration of foreign DNA following microinjection of tobacco mesophyll protoplasts", Mol. Gen. Genet. vol. 202, pp. 179-185, 1986.
Klein T.M. et al., "High-velocity microprojectiles for delivering nucleic acids into living cells", Nature, vol. 327, pp. 70-73, 1987.

\* cited by examiner

SEQUENCE LISTING

```
<160> NUMBER OF SEQ ID NOS: 34

<210> SEQ ID NO 1
<211> LENGTH: 921
<212> TYPE: DNA
<213> ORGANISM: Artificial Sequence
<220> FEATURE:
<223> OTHER INFORMATION: Bombyx mori_SDR

<400> SEQUENCE: 1
atgtccgtct cacgcctggt cgctgtgacc gggtgcgata gtggacttgg ctgggcggtc      60
gcagcccgac tggcccgcga aggtttcatc accatcgccg gtatgcacaa aggaatagag     120
accgaagcag ccaaagccct cgagaaactc tgcgcacaca cgttcccccct cgacgtgact     180 cgtgtggaga gcgttcagga attccggaag tacgtgctta ccgtcttgaa ggataaccct     240
aagtacaaat tccacgccgt ggtcaacaac gctggagtca tgacagttgg aaagtacgag     300
tggatgacag cctcgatgat tgagagcccg gtacatgtga atctcctcgg cgcgatgaga     360
gtcatctccg cgtttcttcc agagatccgg aagacggcaa tcgagactac aagcaaacct     420
aagcccagga tcatcaacgt cggttcgcat tgcggcctgc agcctttgcc cgccttcgct     480
gcatacagtg cgtcaaaagc tggccttctc gcgttgacaa ggtgtctaca tcttgagcac     540
agcgagcacg ggctggcggt gattgccttc gttccaggcg gcttcgtcgg ctcttctaac     600
attctgctgg ggcaggaaac caagggcgaa gccatggttg agcatttgaa cgacgagcaa     660
cgcaagttct acgggaataa gatagagtct ctaaacaatt acctggagct ggcttcgggc     720
gaagggaagt tcgactccat gcatgacatg aagatactta acacgtttat gaaggcgatg     780
ctggacgaga ctccgaagtt aatgtacaag gtggaatcct ggcgctatat gttttattat     840
aatctcatga gacttccatt gccgctcttt atccacaagt ggattatcaa gcagtttctc     900
```
agcttcccgg atcaccaatg a                                        921

<210> SEQ ID NO 2
<211> LENGTH: 1611
<212> TYPE: DNA
<213> ORGANISM: Artificial Sequence
<220> FEATURE:
<223> OTHER INFORMATION: Bombyx mori_C-14 hydroxylase

<400> SEQUENCE: 2
atgagttcgc tcatcattgt gttttttcgtt ttcgctttgg cggtttataa actgcttaga    60
cgcaagaccg agaggtgggt gaagacgaat aagtatggcg agtcgagac cgcaatcctc    120
aggaccgcac ctgggcccgt tgctggcca attatcggga gtctacacct tctgggcggc    180
cacgagtcgc cctttcaggc cttcactgag ctgtcgaaga aatacggcga cattttttagc    240
gtgaaattgg gcagcgccga ctgcgtggta gttaacaatt tatctctcat cagggaagtt    300
cttaatcaaa atggcaacgt ggtggcagga cgaccggatt tcctgcgctt ccataagctc    360
ttcgccggcg atcggaataa ctctctggct ctgtgcgact ggtcaaatct tcagctgcgc    420
cgcaggaacc tggcgaggcg ccactgcggt cccaagcagc acacggactc ctacgcccgc    480
atcggcaccg taggcaccct tcgaatctgtc gagctaattc aaacccttaa gggattgact    540
agcagatctg atgctagcat cgatctaaag ccgatcctga tgaagtccgc catgaatatg    600
ttctcaaact atatgtgtag cgtccgtttt gatgacgaag atttggagtt ccagaagatt    660
gtcgatcact cgacgagat cttctgggaa atcaaccagg gctacgctgt cgattttctg    720
ccgtggctgg cgccttttcta caagaagcac atggagaagc tctccaactg gagtcaggac    780
atccgatcct tcatcctgtc aaggatcgtg gagcaacgcg agataagcct cgacacggaa    840
gctccggaga aggattttct ggacggcctc ctcagggtgc tccacgaaga ccctactatg    900
gataggaaca ctattatctt catgctcgaa gacttcctcg gggggcattc gtctgttggt    960
aacttagtga tgctgtgtct gactgcagtc gcccgggacc cagaggtggg aaggaagata   1020
cgtcaggaga tcgacgcggt gaccagaggc aagcggcccg taggtttgac cgatcgtagc   1080
catttgccgt acacagaggc caccatcctc gagtgcctcc ggtacgcctc ctccccgatc   1140
gtcccacacg tggccaccga gaatgctaat atatccgggt acggaatcga aagggtact   1200
gtcgttttca tcaacaacta cgttctgaac aattcagagc agtatgggtc agagcccgag   1260
aagtttgacc caagccgttt tctggaaaag acacgcgtga ggacacgccg caactcccaa   1320
tgtgattccg ggctcgagtc cgactcggag cgggcaccag tcggcaagcc tgacgtcgag   1380
agagagatgc ttagtgtgaa aaagaacata ccccattttca tacctttcag cattggtaag   1440
agaacgtgca ttggtcagac aatggtcacg tcaatgtcgt tcacgatgtt tgcgaacatc   1500
atgcagtcct ttgaagtcgg agttgagaac atcaacgacc tccgacaaaa gccggcgtgc   1560
gtggcgctac caaaaaacac atacaagatg catttgatac ctcggaagtg a            1611

<210> SEQ ID NO 3
<211> LENGTH: 1617
<212> TYPE: DNA
<213> ORGANISM: Artificial Sequence
<220> FEATURE:
<223> OTHER INFORMATION: Bombyx mori_C-25 hydroxylase

<400> SEQUENCE: 3
atggaccttt attttatttg gctggtaacg ttcgtggccg ggttttggat tttcaaaaag    60

-continued

| | |
|---|---|
| ataaaggaat ggcagaatct cccccccgga ccttgggggc tacccatcgt cggctatttg | 120 |
| cctttcatcg atcgctacca cccacatatt accttgacaa acttgtccaa gacatacggc | 180 |
| gcgatttacg gactcaaaat gggcagcatt tacgccgtcg tgttaagcga tcacaagctt | 240 |
| gttggggata cgttctcaaa agattcattt tctggacggg ctcctctgta cctcacccac | 300 |
| ggccttatga acggtaatgg cattatttgt gccgaaggcg gtttgtggag ggaccaaagg | 360 |
| aaactcataa caagctggtt gaagagtttt ggaatgtcca agcactccgt ttcccgagaa | 420 |
| aaactagaga agcgaatagc tagcggggta tacgaaatct tggagaacat cgaaaagacc | 480 |
| tctgatgctg cattggatct tcctcacatg ctgacgaact ctttaggaaa cgttgtcaac | 540 |
| gagataatat tcggattcaa gtttccaccg gaagacaaga cctggcaatg gttccgccaa | 600 |
| atccaggagg agggatgcca tgagatggga gtcgcagggg ttgtaaactt cctgcccttc | 660 |
| atacgccatg tctcgccaag cacccgaaaa acaatcgaag ttctcgtccg tggccaggca | 720 |
| cagacgcata ctctctacgc cagcatgatc gacagaagga ggaagatgtt gggcctcgag | 780 |
| aagcccaagg gagccgaata tgctcctcat gaaaatcttc tcaagctgta tccaaatggc | 840 |
| catatcaagt gcataaagta cagcaaagtc tctccgaaca ccgagcattt cttcgatccc | 900 |
| aacactttga tcccgactga aggcgattgc attctgacaa cttcctgtt ggagcagaag | 960 |
| aagcgattcg agagtggtga cccgacggcg ctgtatatga gagacgaaca gttacacttt | 1020 |
| ctactcgcgg acatgttcgg cgccggcctg gataccacat cggtgaccct ggcgtggttt | 1080 |
| ctgctataca tggcgttgtt cccagaagag caggaggaaa tccgcaaaga aatcctttcc | 1140 |
| gtatatccat atgacgatga tgttgattcg tccaggctgc ctcttcttat ggcggcaatc | 1200 |
| tgtgagactc agaggattcg aagcattgtt ccagtgggca tcccgcacgg ttgcatcgag | 1260 |
| gacgcgtacc tggcaattaa cagaatcccc aagaatgcca tggtgatccc cttgcaatgg | 1320 |
| gctatacaca tggacccgaa tgtctgggaa gagccagaaa agttcaaacc gaggcggttt | 1380 |
| ttggctcagg acgttcccct gcttaagcct caagaattca ttccgttcca aactgggaag | 1440 |
| cggatgtgtc cgggtgacga gctgtcccgt atgttgtcgt gcggcctcgt tagtcgccta | 1500 |
| ttcagaaagc agcgtattcg actcgcctca aaaataccga cagcagagga gatgcgtgga | 1560 |
| accgtcggtg tgacgttggc ccctcctccg gtgaagtact actgcgagcc aatttga | 1617 |

<210> SEQ ID NO 4
<211> LENGTH: 1554
<212> TYPE: DNA
<213> ORGANISM: Artificial Sequence
<220> FEATURE:
<223> OTHER INFORMATION: Bombyx mori_C-22 hydroxylase

<400> SEQUENCE: 4

| | |
|---|---|
| atgttcgtta ggctcaccgt taagaacaac atcccctacc gggctaggaa gtgcgtgtac | 60 |
| aggagagcgt ccgagaactt tgtggggtct gagcatgcca gtaaggtcaa tgaacagggc | 120 |
| gataacctca tgaacttcga agacatccca ggaccacgga gctatcctat tattgggacg | 180 |
| ctccataaat acctacctct gatcggggac tatgacgccg aagctttaga taagaatgca | 240 |
| atccttaatt ggcgacggta tggtagctta gttcgggaaa accgatagt caatctggtc | 300 |
| cacgtttatg atccggacga cattgaggcc gtgttccgac aggaccaccg ctatccagca | 360 |
| aggcgctcgc atacagcgat gaactactac agaaccaaca agccaaacgt gtacaatact | 420 |
| ggcggactgc ttgcgaccaa cggacccgac tggtggagac tcagaagcat attccaaaaa | 480 |
| aacttcactt cgccacagtc cgtgaagact cacgtctcgg acaccgacaa tatcgccaag | 540 |

```
gagttcgtcg agtggatcaa gcgcgacaag gtgtcatcta agaacgattt cctcacgttt      600
ctaaatcgcc ttaatctcga aatcataggt gtggtcgcgt ttaacgagcg cttcaactct      660
ttcgctctga gcgagcaaga ccccgagagt cgcagcagca agacgatcgc ggctgcattc      720
ggatcaaatt ctggggtcat gaagctcgac aaaggattcc tctggaaaat gttctctact      780
ccactataca agaaactcgt gaatagccag atctacctgg aaaaaatttc cacagatatt      840
ttgatcagaa agattaacct ctttgaatcc gatgattcga aaaacgataa atcgttgctg      900
aaaaccttcc ttcagcaacc ccagctcgac cacaaggata ttatgggaat gatggtcgat      960
atcctgatgg ctgcaatcga cacaacagcc tacacgacca gcttcgtctt gtaccatata     1020
gccaggaaca agagatgcca ggacgaaatg tttgaggagt tgcacacatt attaccgaag     1080
aaagatgatg agatcaccgc cgacgttctt tctaaagctt catacgtgag gagcagtatc     1140
aaggagtcct tgcgcctaaa cccggtatcc ataggcatcg gtcgttggct gcagaaggac     1200
atcgtattaa agggatactc catccccaag ggaactgtta tagtgacgca gaacatgacg     1260
tcatccaggt tgccgcagtt tatacgggac cccttaacct tcaaacctga gaggtggatg     1320
cgtggttcac cgcaatacga gaccattcac ccgttcctga gcttgccttt tggtcacggg     1380
ccccgttcgt gtattgcaag aagactggcc gagcaaaata tttgcattat cttaatgagg     1440
ttaattcgtg agtttgagat ccaatgggcc ggcgaggaac ttggagtgaa gacactgctt     1500
ataaataaac caaacaagcc tgtatcactc aacttcatcc aagaagttc ctga           1554

<210> SEQ ID NO 5
<211> LENGTH: 1461
<212> TYPE: DNA
<213> ORGANISM: Artificial Sequence
<220> FEATURE:
<223> OTHER INFORMATION: Bombyx mori_C-2 hydroxylase

<400> SEQUENCE: 5
atgcatcgct tcccgtctat gtcttccatc cgatccgccg ttaggagtcg caacagtaac       60
aggtgctcga tgtcaaccaa accgcacaag agcctccgta ccatcgatga gatgccacat      120
aagaagtcgc tcccaatcat cggaacaaaa tttgacttat tctcagcagg gggggcaaa       180 aaccttcaca agtatatcga catgcgtcac aagcagttag gccctatatt ctacgagcgg      240
ctcaccggca agaccaaact tgtcttcatc agcgaccca ctcacatgaa aagcctgttc       300
ctgaatctag aaggcaaata tccggcccat atcctgccag aaccgtgggt tctgtatgag      360
aagctttacg gatccaagcg cggcctttttc ttcatggacg gagaggactg gttgattaat      420
cggaggatta tgaacaaaca ccttctccgc gaagattcag atgtgtggtt aagggctccc      480
attagaacgg ctgtgttcca ctttatctgc aactggaagc ttcgcgcaca gagcggcaac      540
ttctctccta acttagaaag cgagtttttac cgcttttcca cggacgttat tttagcagtc      600
cttcaaggga atagtgccct attaaagccc acgccagagt acgagatgtt gctgctgctg      660
ttttcggagg ctgtcaagaa gatattctca accactacca aattatatgc tttgcccgta      720
gaattctgcc agcgatggaa cttaaaggtg tggcgcaact tcaagcaatc cgtcgatgat      780
tccatctcca tcgcgcagaa aattgtatac gagatgttgc acacaaaaga cgctggtgac      840 ggttggtga agagactaaa ggatgagaac atgagcgatg agttataaac gcggattgtt       900
gctgacttcg tcatcgccgc gggtgacacg acagcttaca caagcctttg gatcttatttt      960 ttactttcaa ataatactga aatcttaacc gaaatgaacg acaatgacca atacgtgaaa     1020
```

```
aacgtggtta aggaagcgat gcgcttatac cctgtcgcgc cattccttac aaggattta    1080 cccaaacaat gtgtcttggg accttacttg ctcgaggaag ggactccggt gattgcctca    1140
atctatacct cgggccgaga cgagcagaat tttagcaagg cggaccagtt tcttccttac    1200
agatgggata ggaatgacca gcgtaaaaag gatttagtga atcatgtgcc gtctgccaca    1260
ctcccattcg cattcggtgc ccggtcgtgt atcggcaaaa agatggctat gttgcaaatg    1320
acggaactca tcagtcagat cgtgaaaaac tttgacctga agtctatgaa caactccgac    1380
gtggatgctg taacttccca ggtgttagtg ccgaacaagg acatcaaagt tttaatacta    1440
ccgcgcagca tttctaagtg a                                              1461

<210> SEQ ID NO 6
<211> LENGTH: 1551
<212> TYPE: DNA
<213> ORGANISM: Artificial Sequence
<220> FEATURE:
<223> OTHER INFORMATION: Bombyx mori_C-20 hydroxylase

<400> SEQUENCE: 6
atgtctctcc cgggagtttt cctgttttcg cactatgttg agagcttttg gtccacaagc     60
cccccgctgc tggactggtc gtgtgttccc acgctggtgc tcgccgtcat cgcagtggtt    120
gttgccgtga ccgcgctcct aacgagaaca tcggatgcta agcactcgtg ccgtttaccc    180
ggcccacagc ctcttccctt cctgggcacc aggtggctct tctggagcag gtacaagatg    240
aacaagctgc acgaggctta tgcagatatg ttcaaacgtt atgggcctgt tttcatggag    300
acgacgcctg gcgcgtcgc cgtggtgtcg atagccgagc ggactgcgct tgaggccgta    360
ctgcgctctc ctgctaagaa gccctaccgt ccgcccactg agatcgtgca aatgtaccgc    420
cgcagcagac ccgacaggta cgcgtcgact ggcctcgtca atgagcaggg cgaaaagtgg    480
taccacttac ggcgcaactt gactaccgat ctcacgagtc cacatacaat gcagaacttc    540
cttccccagt tgaacaccat ctccgatgac ttccttggag ctactcaatac atctaggcag    600 tctgatggca cagtctacgc cttcgaacag ctgacgaaca gaatgggtct ggagtcggta    660
tgcggtctga tgctggggttc aagacttggg ttttctcgaac gatggatgag cgggcgggca    720
atggctctgg ccgcggctgt caagaaccac tttcgagcgc agagggactc ttattacgga    780
gcgccgttat ggaaatttgc gcctacagcg ctctacaaga cgttcgtcaa gagcgaggaa    840
actatacacg cgattgtcac agagctgatg gaggaggcca aatccaaaac cactgggatg    900
gcccaagacg aggcaatcca ggagattttc cttaaaatac ttgaaaaccc agcactggac    960
atgcgcgaca agaaggctgc cattatcgac ttcataaccg ccggcattga ccctagcc    1020 aatagtttgg tgttcctcct gtacttgctg agtggacggc cagattggca agaaagatc    1080 aattccgagc tcccaccgta cgctatgctt tgctccgagg atttggctgg cgcaccttcg    1140
gtcagagctg cgatcaatga agccttagaa ctattgccaa ccgccccatt tctagcaagg    1200
ctcttagatt caccgatgac gactgggggt cataaaatcc cgcctggaac ctttgtgctc    1260
gcccacaccg cggcggcttg tcgcagagaa gaaaacttct ggcgcgccga ggaatatctt    1320
ccggagcgat ggattaaagt gcaggagccg catgcctact cgctagtggc tccattcgga    1380
cgcgggcgca ggatgtgccc gggcaaacgg tttgtagaac tcgagctaca tctcctcctc    1440
gcaaagatca tgcaaaaatg gcgggtggag ttcgacggtg aactggacat tcaattcgac    1500
ttcctcctgt cagcaaagtc accagttacc ttgcgtcttg tcgagtggtg a             1551
```

<210> SEQ ID NO 7
<211> LENGTH: 1008
<212> TYPE: DNA
<213> ORGANISM: Artificial Sequence
<220> FEATURE:
<223> OTHER INFORMATION: Drosophila melanogaster_SDR

<400> SEQUENCE: 7

| | |
|---|---|
| atgagcggca gtcaacttct ccgcgccctg aggcgatccc tgggacttgg caggcaacag | 60 |
| ctgaaggtcg attcgcggca cgtcgtgctc atcaccggct gcgattcggg attgggccac | 120 |
| tccatggccg tttactgcca tgagtcgtta catatgaccg tgatttcctg ctgtcacaac | 180 |
| atcaagtctg agggagctaa actccttcag ggcctagcgt ctgcgaagga cgggctgagc | 240 |
| agaatgcaca cattggagtt ggacctcttg aacccgatt ccattcgcct tgtccatagg | 300 |
| caactaaggg acatactggc caaggacccc tcttaccggc tgacggcact gataaacaat | 360 |
| gctggagtaa tgtgctttgg ggaattcgag tgcagctaa cggagcaaat cgaggcgcag | 420 |
| atcaactgca acctgttggg cactatgagg ttaacacatg aactgctgcc gctcctccgg | 480 |
| cagcagcagg gcaggatcat caatgttact agccactgtg ggctccaggc tctgccggca | 540 |
| ctgggtcctt acgcggcctc caaggcagcc cttcgcttct ggacagattc actccgcgtt | 600 |
| gaactgcagc agtatgggat ggaggtggtg aacttcatac caggctcctt cgtcctggac | 660 |
| agcaacattg cggcaagaca acagcagcac gctcaaaaga tgcgagaggc ctttagtgcc | 720 |
| gagcagcacg ctctgtacga cacctatttc gaggccttca tggttatct aaaagtcctg | 780 |
| tctggtttca gccgccaaa ccggctgagg aacgaaagcc ttctggcaaa gtttaaagac | 840 |
| gctttgacca gctcacaacc tttggcccct tacatcgagg aacctcgtag ataccgcctc | 900 |
| taccgctggc tctttacgct ctgccccact ccgctcgtgg attggctcac cgtgcgtttc | 960 |
| tgtgcgatgc caacctacga gtcaacgaat agacaggaga agatttga | 1008 |

<210> SEQ ID NO 8
<211> LENGTH: 1632
<212> TYPE: DNA
<213> ORGANISM: Artificial Sequence
<220> FEATURE:
<223> OTHER INFORMATION: Drosophila melanogaster_C-14 hydroxylase

<400> SEQUENCE: 8

| | |
|---|---|
| atgctggctg ctctgatcta cactattttg gcgattttac tgagtgttct cgccacctcc | 60 |
| tacatctgca tcatatacgg cgtcaagcgc cgcgttctgc aacccgttaa aacaaagaat | 120 |
| tcaactgaga tcaaccacaa cgcttaccaa aagtataccc aggcccccggg accgcgacca | 180 |
| tggcccatca ttggtaacct ccacctgctc gaccgctacc gcgacagccc ctttgcgggc | 240 |
| ttcacggcgc tcgcacagca atacggtgac atatattcgc tgaccttcgg acacacccgc | 300 |
| tgtcttgtgg tgaacaacct cgagctgatc cgcgaggttc tcaaccaaaa cggcaaggtg | 360 |
| atgagcgggc ggccagactt catacgatac cataagctat tggtggcga gcggagtaat | 420 |
| tcgttggctc tgtgcgattg gtcacagctg cagcagaagc gtaggaatct ggccaggcgt | 480 |
| cactgcagcc ccagggaatt ttcctgcttc tacatgaaga tgtcccagat tggttgcgag | 540 |
| gagatggagc actggaaccg cgagctcggc aaccaacttg ttcctgggga ccgatcaac | 600 |
| atcaagcccc tgattctgaa ggcgtgtgca acatgtttta gtcagtacat gtgctcgttg | 660 |
| agattcgact acgatgatgt ggacttccaa cagattgtgc agtacttcga cgagatattc | 720 |
| tgggaaatca atcagggcca cccgctggat tttctccct ggttgtatcc cttctaccag | 780 |

| | |
|---|---|
| cgccacctca acaagatcat caattggtcc tcgactatca ggggcttcat aatggagagg | 840 |
| attatccggc atcgcgagct gagcgtcgac ctcgatgaac cagataggga cttcacagat | 900 |
| gctcttctta aaagcctgct tgaggataag gatgtctccc ggaacactat tatcttcatg | 960 |
| ctggaggact tcataggtgg acattccgcg gttggcaatc tagtcatgct tgtgctggcc | 1020 |
| tatatagcca aaaacgtgga cattgggagg agaattcaag aggaaatcga cgcaattatt | 1080 |
| gaagaggaaa ataggtcaat taatttgctc gacatgaacg ccatgcccta cacgatggcg | 1140 |
| acgattttcg aggtgctgcg gtactcatcc tccccgatcg ttccacatgt ggccaccgag | 1200 |
| gacacagtga tctcgggcta tggggtaacc aagggcacca tcgtgttcat caacaactat | 1260 |
| gtcctcaaca ccagcgagaa gttctgggta atcccaagg agtttaaccc tttaagattt | 1320 |
| ttggaaccgt caaaggaaca gagccctaaa aactccaaag ggtctgattc tgggatcgaa | 1380 |
| agtgacaacg agaaattaca actaaagcgc aatataccgc acttcctgcc cttcagcatt | 1440 |
| gggaagcgga cttgcatcgg ccagaatctc gtgagaggct tcggatttct ggtcgtggtc | 1500 |
| aacgtgatgc agagatataa tatcagcagc cataacccct tcgacgataa gatctctccg | 1560 |
| gagtctcttg cactgccagc cgactgtttt ccattggtct tgacacccag ggagaagatc | 1620 |
| ggaccactat ga | 1632 |

<210> SEQ ID NO 9
<211> LENGTH: 1725
<212> TYPE: DNA
<213> ORGANISM: Artificial Sequence
<220> FEATURE:
<223> OTHER INFORMATION: Drosophila melanogaster_C-25 hydroxylase

<400> SEQUENCE: 9

| | |
|---|---|
| atgtcagcgg acatagtcga tattggccac accggttgga tgccctctgt tcaatccctg | 60 |
| agtatactgc tggttcctgg tgcgctcgtc ttagtaattc tctacctgtg cgagagacag | 120 |
| tgtaatgatc tcatgggtgc accaccgccg ggaccatggg gcctgccctt tctcgggtac | 180 |
| ctgccctttc tggacgcccg tgcgccgcac aagtcgctcc agaaactcgc caagcggtat | 240 |
| ggtggcattt tcgaacttaa aatgggcagg gtgccgactg tagtcctttc tgatgctgcc | 300 |
| ttggttagag atttctttag aagggatgtg atgactggcc gtgcaccccct ctacctaacc | 360 |
| cacggcatca tggggggatt tggcatcatc tgcgctcaag aggacatttg gcgacatgct | 420 |
| cggcgcgaga caatcgattg gctaaaggcg ttgggcatga ccagacggcc ggggggaactg | 480 |
| agggcgcggc tggagcgtag gatagccagg ggagtcgacg agtgcgtacg gcttttcgat | 540 |
| actgaggcaa gaagagctg tgcgtcggaa gtgaatccgc tgcctgcgtt acatcactcg | 600 |
| ctgggcaaca ttatcaacga cttagtcttc gggatcacct acaagcgcga cgaccccgat | 660 |
| tggctgtact tacagcggct gcaagaggag ggcgtcaagc tgattggcgt cagcggggtg | 720 |
| gtcaactttc tcccgtggct gagacactta ccagccaacg ttcgcaatat acgctttcta | 780 |
| ctggagggta aggccaaaac gcacgccatc tatgacagaa ttgtggaggc ctgtggccag | 840 |
| cgcctcaagg agaagcagaa agtgttcaag gaactccagg aacagaagcg cctccaaagg | 900 |
| cagcttgaaa aggaacaatt gaggcagtca aagaagcgg atccaagcca ggagcaaagt | 960 |
| gaagcagacg aagacgacga agaaagcgat gaggaagaca catacgagcc agagtgcatc | 1020 |
| cttgagcact cctcgcagt tagagacacg gattcacagc tctactgcga cgaccagttg | 1080 |
| aggcatctgc tggccgatct ctttggagct ggggtgaca cctccctggc caccctctcgc | 1140 |
| tggttcctgc tctacttggc acgcgagcaa agatgccagc ggcgcctgca tgagcttctc | 1200 |

```
ctgccgttgg gtccgtctcc cactttggag gaactggagc cactggctta cctaagggca    1260
tgcatttccg agacgatgcg tatcaggagc gttgtccctc taggcatacc gcatggatgc    1320
aaggagaact tcgtcgtggg cgattatttc atcaagggtg ggtcgatgat cgtttgctct    1380
gaatgggcta ttcacatgga cccagtggcc ttccctgaac ctgaagagtt tcgtccagag    1440
cgcttcttga ccgccgatgg agcctatcaa gcgcctccac agttcatccc tttcagctcc    1500
ggctatagga tgtgtcccgg cgaagaaatg gctagaatga tactcacgct cttcacgggg    1560
cgcatcctca ggcgcttcca tttggaactg ccttccggca ctgaggtgga tatggctggt    1620
gagtcaggca tcacactgac ccccacaccg cacatgctgc gattcacaaa attgccggcg    1680
gtggagatgc gacatgcacc cgacggagct gtggttcagg actga                   1725
```

<210> SEQ ID NO 10
<211> LENGTH: 1725
<212> TYPE: DNA
<213> ORGANISM: Artificial Sequence
<220> FEATURE:
<223> OTHER INFORMATION: Drosophila melanogaster_C-22 hydroxylase

<400> SEQUENCE: 10

```
atgtcagcgg acatagtcga tattggccac accggttgga tgccctctgt tcaatccctg      60
agtatactgc tggttcctgg tgcgctcgtc ttagtaattc tctacctgtg cgagagacag     120
tgtaatgatc tcatgggtgc accaccgccg ggaccatggg gcctgcccct tctcgggtac     180
ctgccctttc tggacgcccg tgcgccgcac aagtcgctcc agaaactcgc caagcggtat     240
ggtggcattt tcgaacttaa aatgggcagg gtgccgactg tagtcctttc tgatgctgcc     300
ttggttagag atttctttag aagggatgtg atgactggcc gtgcaccccct ctacctaacc     360 cacggcatca tgggggggatt tggcatcatc tgcgctcaag aggacatttg gcgacatgct    420
cggcgcgaga caatcgattg gctaaaggcg ttgggcatga ccagacggcc gggggaactg    480
agggcgcggc tggagcgtag gatagccagg ggagtcgacg agtgcgtacg gcttttcgat    540
actgaggcaa agaagagctg tgcgtcggaa gtgaatccgc tgcctgcgtt acatcactcg    600
ctgggcaaca ttatcaacga cttagtcttc gggatcacct acaagcgcga cgaccccgat    660
tggctgtact acagcggct gcaagaggag ggcgtcaagc tgattggcgt cagcggggtg     720
gtcaactttc tcccgtggct gagacactta ccagccaact tcgcaatat acgctttcta    780 ctggagggta aggccaaaac gcacgccatc tatgacagaa ttgtggaggc ctgtggccag    840
cgcctcaagg agaagcagaa agtgttcaag gaactccagg aacagaagcg cctccaaagg    900
cagcttgaaa aggaacaatt gaggcagtca aagaagcgg atccaagcca ggagcaaagt    960
gaagcagacg aagacgacga agaaagcgat gaggaagaca catacgagcc agagtgcatc    1020
cttgagcact cctcgcagt tagagacacg gattcacagc tctactgcga cgaccagttg    1080
aggcatctgc tggccgatct ctttggagct ggggtggaca cctccctggc caccettcgc    1140 tggttcctgc tctacttggc acgcgagcaa agatgccagc ggcgcctgca tgagcttctc    1200
ctgccgttgg gtccgtctcc cactttggag gaactggagc cactggctta cctaagggca    1260
tgcatttccg agacgatgcg tatcaggagc gttgtccctc taggcatacc gcatggatgc    1320
aaggagaact tcgtcgtggg cgattatttc atcaagggtg ggtcgatgat cgtttgctct    1380
gaatgggcta ttcacatgga cccagtggcc ttccctgaac ctgaagagtt tcgtccagag    1440
cgcttcttga ccgccgatgg agcctatcaa gcgcctccac agttcatccc tttcagctcc    1500
```

```
ggctatagga tgtgtcccgg cgaagaaatg gctagaatga tactcacgct cttcacgggg    1560
cgcatcctca ggcgcttcca tttggaactg ccttccggca ctgaggtgga tatggctggt    1620
gagtcaggca tcacactgac ccccacaccg cacatgctgc gattcacaaa attgccggcg    1680
gtggagatgc gacatgcacc cgacggagct gtggttcagg actga                    1725

<210> SEQ ID NO 11
<211> LENGTH: 1563
<212> TYPE: DNA
<213> ORGANISM: Artificial Sequence
<220> FEATURE:
<223> OTHER INFORMATION: Drosophila melanogaster_C-2 hydroxylase

<400> SEQUENCE: 11
atgaccgaga agagggagag gccgggcccg cttcgctggc tgagacacct gctcgaccaa      60
ctcctggtcc gaatccttag cctatccctc ttcaggtcgc gctgcgaccc gcctccactt     120
cagcgttttc ccgcaacgga actaccgcct gccgtcgccg ctaaatacgt gcctatccct     180
agggtgaagg gactgcccgt agttgggaca cttgtggatc ttatagcagc cggcggagcc     240
actcaccttc ataagtacat cgacgcgagg cacaagcagt atggcccaat tttccgcgag     300
cgtctcggcg gcacccaaga tgcagtcttc gtttcgagcg caaatctcat gcgcggagtc     360
ttccaacacg aggggcagta tccgcagcac ccgttgccgg atgcctggac gctgtataac     420
cagcaacatg cttgccaaag gggactgttc ttcatggagg gcgcggagtg gctgcataac     480
agacgcatac tcaatagact gctgctcaac gggaatctga attggatgga tgtgcacatt     540
gagagctgta ccagaaggat ggtggatcag tggaaaagac gcactgcgga ggcggctgcg     600
attcccctag cggagtctgg tgagatccga agttacgaac tgcccctgct cgaacaacag     660
ctctaccgtt ggtctataga agttctgtgc tgcatcatgt ttggcacttc agtgctcacc     720
tgcccaaaga tccagtcctc gctcgactac ttcacgcaga ttgttcacaa ggtgttcgag     780
cattcgtcca ggctaatgac attcccccct cgcttggccc agattttgcg cttacccatc     840
tggcgggatt tcgaagccaa cgttgatgag gtgctcaggg aaggagccgc cattatcgat     900
cattgtatca gagtgcagga ggaccaaagg agaccacatg acgaggcgct ttaccatcgc     960
ctccaagcgg ccgacgtccc aggcgatatg atcaagcgca tattcgtcga cttggtcatt    1020
gctgcaggtg acacgaccgc attcagcagt cagtgggctt tgtttgccct ttcaaaagaa    1080
ccgaggttac agcaacgcct cgctaaggag agagctacaa acgattctcg cttgatgcat    1140
ggcctgatca aggaatccct gcgactgtac cccgtagctc cctttattgg gcggtatctt    1200
cctcaggatg ctcaacttgg cggtcacttt atcgaaaagg ataccatggt cctattatcc    1260
ttgtacactg caggtcgcga tccatcacac tttgagcaac cggaacgtgt gctcccggag    1320
cgctggtgca tcggtgagac agaacaggtg cacaaatcac acggcagtct gcctttcgcc    1380
atcgggcagc ggtcttgcat aggtcgccgt gttgcactca gcagctgca ctccttgctt    1440 ggccgatgtg ctgctcagtt tgagatgagc tgccttaacg atatgcctgt tgatagcgta    1500
ctcaggatgg tcaccgtgcc agatcggact ttgaggttag ccctccggcc acggacagag    1560
tga                                                                  1563

<210> SEQ ID NO 12
<211> LENGTH: 1563
<212> TYPE: DNA
<213> ORGANISM: Artificial Sequence
<220> FEATURE:
<223> OTHER INFORMATION: Drosophila melanogaster_C-20 hydroxylase
```

<400> SEQUENCE: 12

```
atgaccgaga agagggagag gccgggcccg cttcgctggc tgagacacct gctcgaccaa      60
ctcctggtcc gaatccttag cctatccctc ttcaggtcgc gctgcgaccc gcctccactt     120
cagcgttttc ccgcaacgga actaccgcct gccgtcgccg ctaaatacgt gcctatccct     180
agggtgaagg gactgcccgt agttgggaca cttgtggatc ttatagcagc cggcggagcc     240
actcaccttc ataagtacat cgacgcgagg cacaagcagt atgcccaat tttccgcgag      300
cgtctcggcg gcacccaaga tgcagtcttc gtttcgagcg caaatctcat gcgcggagtc     360
ttccaacacg aggggcagta ccgcagcac ccgttgccgg atgcctggac gctgtataac      420
cagcaacatg cttgccaaag gggactgttc ttcatggagg gcgcggagtg gctgcataac     480
agacgcatac tcaatagact gctgctcaac gggaatctga attggatgga gtgcacatt      540
gagagctgta ccagaaggat ggtggatcag tggaaaagac gcactgcgga ggcggctgcg     600
attccctag cggagtctgg tgagatccga agttacgaac tgcccctgct cgaacaacag      660
ctctaccgtt ggtctataga agttctgtgc tgcatcatgt ttggcacttc agtgctcacc     720
tgcccaaaga tccagtcctc gctcgactac ttcacgcaga ttgttcacaa ggtgttcgag     780
cattcgtcca ggctaatgac attccccct cgcttggccc agattttgcg cttacccatc      840
tggcgggatt tcgaagccaa cgttgatgag gtgctcaggg aaggagccgc cattatcgat     900
cattgtatca gagtgcagga ggaccaaagg agaccacatg acgaggcgct ttaccatcgc     960
ctccaagcgg ccgacgtccc aggcgatatg atcaagcgca tattcgtcga cttggtcatt    1020
gctgcaggtg acacgaccgc attcagcagt cagtgggctt tgtttgccct ttcaaaagaa    1080
ccgaggttac agcaacgcct cgctaaggag agagctacaa acgattctcg cttgatgcat    1140
ggcctgatca aggaatccct gcgactgtac cccgtagctc cctttattgg gcggtatctt    1200
cctcaggatg ctcaacttgg cggtcacttt atcgaaaagg ataccatggt cctattatcc    1260
ttgtacactg caggtcgcga tccatcacac tttgagcaac cggaacgtgt gctcccggag    1320
cgctggtgca tcggtgagac agaacaggtg cacaaatcac acggcagtct gcctttcgcc    1380
atcgggcagc ggtcttgcat aggtcgccgt gttgcactca agcagctgca ctccttgctt    1440
ggccgatgtg ctgctcagtt tgagatgagc tgccttaacg agatgcctgt tgatagcgta    1500
ctcaggatgg tcaccgtgcc agatcggact ttgaggttag ccctccggcc acggacagag    1560
tga                                                                   1563
```

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13

```
caccatgagt tcgctcatca ttgtg                                             25
```

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
tcacttccga ggtatcaaat gcatc                                      25

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
caccatggac ctttatttta tttggctg                                   28

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
tcaaattggc tcgcagtagt acttc                                      25

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
caccatgttc gttaggctca ccgtt                                      25

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
tcaggaactt cttgggatga agttg                                      25

<210> SEQ ID NO 19
<211> LENGTH: 27
<212> TYPE: DNA
<213> ORGANISM: Artificial Sequence
<220> FEATURE:
<223> OTHER INFORMATION: primer

<400> SEQUENCE: 19
caccatgcat cgcttcccgt ctatgtc                                    27

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
tcacttagaa atgctgcgcg gtag                                       24

<210> SEQ ID NO 21
<211> LENGTH: 26
<212> TYPE: DNA
<213> ORGANISM: Artificial Sequence

```
<220> FEATURE:
<223> OTHER INFORMATION: primer

<400> SEQUENCE: 21
caccatgtct ctcccgggag ttttcc                                          26

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
tcaccactcg acaagacgca agg                                             23

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
caccatgagc ggcagtcaac ttctc                                           25

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
tcaaatcttc tcctgtctat tcg                                             23

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
caccatgctg gctgctctga tctac                                           25

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
tcatagtggt ccgatcttct c                                               21

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
caccatgtca gcggacatag tcga                                            24
```

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
tcagtcctga accacagctc c                                              21

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
caccatgttg accaagctgc taaag                                          25

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
tcactcgcga cggaggcgca g                                              21

<210> SEQ ID NO 31
<211> LENGTH: 24
<212> TYPE: DNA
<213> ORGANISM: Artificial Sequence
<220> FEATURE:
<223> OTHER INFORMATION: primer

<400> SEQUENCE: 31
caccatgacc gagaagaggg agag                                           24

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
tcactctgtc cgtggccgga g                                              21

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
caccatggcc gtgatactgt tgctc                                          25

```
<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
tcagaaaacg cgatcgctga g                                           21
```

METHOD FOR PRODUCING TRANSGENIC PLANT HAVING INCREASED CONTENT OF 20-HYDROXYECDYSONE USING INSECT-DERIVED GENE AND PLANT PRODUCED BY THE SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/013177 filed on Nov. 1, 2018, which claims priority to the benefit of Korean Patent Application No 10-2017-0145435 filed in the Korean Intellectual Property Office on Nov. 2, 2017, the entire contents of which are incorporated herein by reference.

TECHNICAL FIELD

The present invention relates to a method for producing a transgenic plant having increased content of 20-hydroxyecdysone using insect-derived gene, and a plant produced by the same method.

BACKGROUND ART

Ecdysteroids are a steroid hormone responsible for the regulation of molting of an insect, and they were first known in 1954. After that, ecdysteroids were discovered first from a plant by Nakanishi and Koreeda in 1966. Ecdysteroids are one group of 2,3,14-trihydroxy-$\Delta$-7-ketosteroids, and they are the compound belonging to polyhydroxylated steroids including known ecdysterones and ecdysones or the like. Although their activity in plant is not fully known, plant ecdysteroids are known to exhibit an influence on a plant defense mechanism as they show an antifeedant effect, avoidance, and insecticidal activity against some non-adapted phytophagous insects.

Meanwhile, plants can be easily transformed and are economically favored as a material for producing proteins in general, and thus they have a great potential for producing peptides and proteins that can be used as a biopharmaceutical (i.e., biopharmaceutical proteins). Until now, most of the biopharmaceutical products have been produced by transformation of cultured mammalian cells, bacteria, fungi, or the like. However, producing a therapeutic protein in plant may yield reduced risk, which is caused by pathogen contamination, and also high production yield compared to the production using mammalian cells, bacteria, fungi, or the like, and, in terms of the quality as well as economic feasibility, it has various advantages like the production in seeds or other storage organs. Furthermore, currently-existing basic facilities and resources can be utilized for the cultivation, harvesting, and storing of transformed grains, and also, as only a relatively small capital investment is required, it is expected that plants are highly useful for commercial production of biopharmaceuticals.

In Korean Patent Registration No. 1526190, "Method for producing a transgenic plant having increased content of 20-hydroxyecdysone using CYP85 gene from spinach and plant according thereto" is disclosed, and in Korean Patent Registration No. 0469139, "Transformed EcR-293 cell line for overexpression of Cdc25B2 or Cdc25B3 by using ecdysone-induced expression system" is disclosed. However, there is no description related to the method for producing a transgenic plant having increased content of 20-hydroxyecdysone using insect-derived gene and the plant produced by the same method as described in the present invention.

SUMMARY

The present invention is devised in view of the above-described needs, and, by collecting the information of 5 kinds of the gene related to the biosynthesis of 20-hydroxyecdysone derived from *Bombyx mori* (silkworm moth) and 6 kinds of the gene related to the biosynthesis of 20-hydroxyecdysone derived from *Drosophila melanogaster* (fruit fly) followed by codon optimization for plant, and introducing the insect-derived genes to a tobacco plant, the inventors of the present invention found that, compared to the wild type tobacco plant, content of 20-hydroxyecdysone has increased in a tobacco plant to which the insect-derived gene related to the biosynthesis of 20-hydroxyecdysone had been introduced, and the present invention is completed accordingly.

In order to solve the problems that are described above, the present invention provides a method for producing a transgenic plant having increased content of 20-hydroxyecdysone compared to a wild type plant including transforming a plant cell with a recombinant vector containing one or more genes encoding one or more proteins of SDR (short-chain dehydrogenase/reductase) protein and C-14 hydroxylase protein; a gene encoding C-25 hydroxylase protein; a gene encoding C-22 hydroxylase protein; a gene encoding C-2 hydroxylase protein; and a gene encoding C-20 hydroxylase protein derived from insect.

The present invention further provides a transgenic plant produced by the above method which has increased content of 20-hydroxyecdysone compared to a wild type plant, and a seed thereof.

The present invention further provides a composition for increasing content of 20-hydroxyecdysone in plant which includes, as an effective component, one or more genes encoding one or more proteins of SDR protein and C-14 hydroxylase protein; a gene encoding C-25 hydroxylase protein; a gene encoding C-22 hydroxylase protein; a gene encoding C-2 hydroxylase protein; and a gene encoding C-20 hydroxylase protein.

The present invention further provides a method for increasing content of 20-hydroxyecdysone in plant including transforming a plant cell with a recombinant vector containing one or more genes encoding one or more proteins of SDR protein and C-14 hydroxylase protein; a gene encoding C-25 hydroxylase protein; a gene encoding C-22 hydroxylase protein; a gene encoding C-2 hydroxylase protein; and a gene encoding C-20 hydroxylase protein derived from insect to overexpress the gene.

The present invention further provides a method for producing a transgenic plant having increased insect resistance compared to a wild type plant by transforming a plant cell with a recombinant vector containing one or more genes encoding one or more proteins of SDR (short-chain dehydrogenase/reductase) protein and C-14 hydroxylase protein; a gene encoding C-25 hydroxylase protein; a gene encoding C-22 hydroxylase protein; a gene encoding C-2 hydroxylase protein; and a gene encoding C-20 hydroxylase protein derived from insect.

The present invention further provides a transgenic plant produced by the above method which has enhanced insect resistance compared to a wild type, and a seed thereof.

The present still further provides a composition for enhancing insect resistance of a plant which includes, as an effective component, one or more genes encoding one or more proteins of SDR protein and C-14 hydroxylase protein; a gene encoding C-25 hydroxylase protein; a gene encoding C-22 hydroxylase protein; a gene encoding C-2 hydroxylase protein; and a gene encoding C-20 hydroxylase protein.

In the present invention, genes derived from *Bombyx mori* for encoding the enzyme related to the biosynthesis of 20-hydroxyecdysone were optimized for plant codon, and expressed in a plant to have increased content of 20-hydroxyecdysone in plant. Because 20-hydroxyecdysone is a material which exhibits an antifeedant effect, avoidance, and insecticidal activity against some harmful insects, an agricultural product with enhanced insect resistance can be developed by using an insect-derived gene related to the biosynthesis of 20-hydroxyecdysone, and also a composition for controlling harmful insects can be developed by using increased 20-hydroxyecdysone. As such, it is believed to have an industrial usefulness.

DETAILED DESCRIPTION

Figure 1:
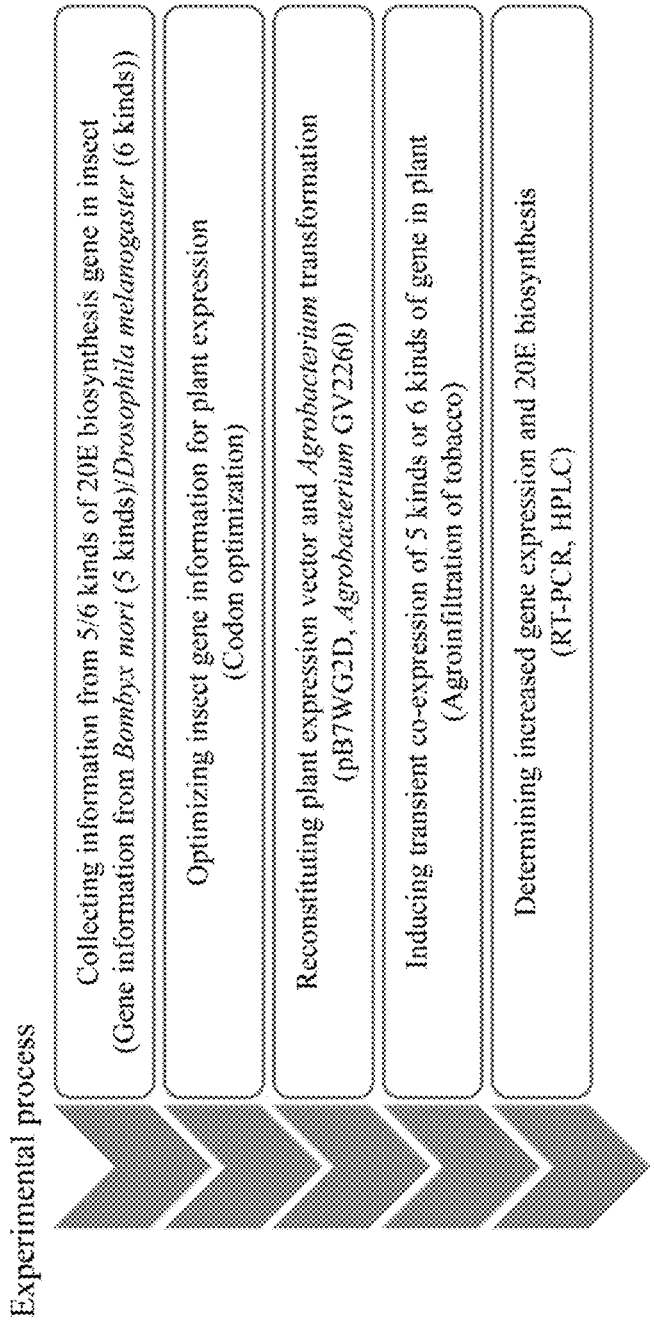
FIG. 1 is a drawing illustrating the experimental process of the present invention.

In order to achieve the object of the present invention, the present invention provides a method for producing a transgenic plant having increased content of 20-hydroxyecdysone compared to a wild type plant including:

transforming a plant cell with a recombinant vector containing one or more genes encoding one or more proteins of SDR (short-chain dehydrogenase/reductase) protein and C-14 hydroxylase protein; a gene encoding C-25 hydroxylase protein; a gene encoding C-22 hydroxylase protein; a gene encoding C-2 hydroxylase protein; and a gene encoding C-20 hydroxylase protein derived from insect; and regenerating a plant from the transformed plant cell.

The SDR, C-14 hydroxylase, C-25 hydroxylase, C-22 hydroxylase, C-2 hydroxylase and C-20 hydroxylase enzymes of the present invention are an enzyme which is related to the biosynthesis of 20-hydroxyecdysone using 7-dehydrocholesterol as a start material.

The enzyme related to the biosynthesis of 20-hydroxyecdysone according to the present invention may be an enzyme derived from an insect such as *Bombyx mori*, *Drosophila melanogaster*, *Manduca sexta*, *Plutella xylostella*, *Musca domestica*, *Tribolium castaneum*, *Anopheles gambiae*, *Aedes aegypti*, *Cluex quinquefasciatus*, *Apis mellifera*, or *Acyrthosiphon pisum*, and preferably an enzyme derived from *Bombyx mori* or *Drosophila melanogaster*, but it is not limited thereto.

In the biosynthetic pathway of 20-hydroxyecdysone, SDR and C-14 hydroxylase are an enzyme related to the conversion step from 7-dehydrocholesterol to ketodiol (2-, 22-, 25-trideoxyecdysone), and SDR and C-14 hydroxylase may act on the conversion step, either separately or together.

According to the production method of the present invention, the recombinant vector may contain a gene encoding SDR, a gene encoding C-25 hydroxylase, a gene encoding C-22 hydroxylase, a gene encoding C-2 hydroxylase and a gene encoding C-20 hydroxylase; a gene encoding C-14 hydroxylase, a gene encoding C-25 hydroxylase, a gene encoding C-22 hydroxylase, a gene encoding C-2 hydroxylase and a gene encoding C-20 hydroxylase; or a gene encoding SDR, a gene encoding C-14 hydroxylase, a gene encoding C-25 hydroxylase, a gene encoding C-22 hydroxylase, a gene encoding C-2 hydroxylase and a gene encoding C-20 hydroxylase, but it is not limited thereto.

The gene encoding SR protein according to the present invention may consist of the nucleotide sequence of SEQ ID NO: 1 or SEQ ID NO: 7; the gene encoding C-14 hydroxylase protein may consist of the nucleotide sequence of SEQ ID NO: 2 or SEQ ID NO: 8; the gene encoding C-25 hydroxylase protein may consist of the nucleotide sequence of SEQ ID NO: 3 or SEQ ID NO: 9; the gene encoding C-22 hydroxylase protein may consist of the nucleotide sequence of SEQ ID NO: 4 or SEQ ID NO: 10; the gene encoding C-2 hydroxylase protein may consist of the nucleotide sequence of SEQ ID NO: 5 or SEQ ID NO: 11; and the gene encoding C-20 hydroxylase protein may consist of the nucleotide sequence of SEQ ID NO: 6 or SEQ ID NO: 12, but it is not limited thereto. Further, homologues of those nucleotide sequences are also within the scope of the present invention. Specifically, the gene encoding SDR, C-14 hydroxylase, C-25 hydroxylase, C-22 hydroxylase, C-2 hydroxylase and C-20 hydroxylase proteins may include a nucleotide sequence which has preferably at least 70%, more preferably at least 80%, still more preferably at least 90%, and most preferably at least 95% sequence homology with the nucleotide sequence of SEQ ID NO: 1 or SEQ ID NO: 7; SEQ ID NO: 2 or SEQ ID NO: 8; SEQ ID NO: 3 or SEQ ID NO: 9; SEQ ID NO: 4 or SEQ ID NO: 10; SEQ ID NO: 5 or SEQ ID NO: 11; and SEQ ID NO: 6 or SEQ ID NO: 12. The "sequence homology %" for a certain polynucleotide is identified by comparing a comparative region with two sequences that are optimally aligned. In this regard, a part of the polynucleotide in comparative region may include an addition or a deletion (i.e., a gap) compared to a reference sequence (without any addition or deletion) relative to the optimized alignment of the two sequences.

The nucleotide sequences of SEQ ID NO: 1 to 6 of the present invention are genes that are derived from *Bombyx mori* while the nucleotide sequences of SEQ ID NO: 7 to 12 of the present invention are genes that are derived from *Drosophila melanogaster*, in which the nucleotide sequences of SEQ ID NO: 1 to 12 are sequences that are optimized for plant codon. The plant may be a maze, but it is not limited thereto.

As described herein, the expression "optimized for codon" means a modification of codon of a polynucleotide encoding a protein with a codon that is used first than others in a specific organism such that the coded protein can be more efficiently expressed in the organism. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene sequence encoding SDR, C-14 hydroxylase, C-25 hydroxylase, C-22 hydroxylase, C-2 hydroxylase and C-20 hydroxylase protein may be inserted to a recombinant expression vector. The expression "recombinant expression vector" means a bacteria plasmid, a phage, a yeast plasmid, a plant cell virus, a mammalian cell virus, or other vector. In general, as long as it can be replicated and stabilized in a host, any plasmid or vector can be used. Important characteristic of the expression vector is that it has a replication origin, a promoter, a marker gene, and a translation control element.

The recombinant vector of the present invention may be a recombinant vector which separately contains a gene encoding insect-derived SDR, a gene encoding insect-derived C-14 hydroxylase, a gene encoding insect-derived C-25 hydroxylase, a gene encoding insect-derived C-22 hydroxylase, a gene encoding insect-derived C-2 hydroxylase, and a gene encoding insect-derived C-20 hydroxylase protein, or a single recombinant vector which contains all of those genes. Preferably, it is a recombinant vector which separately contains each of those genes, but it is not limited thereto.

In the present invention, the expression vector containing the gene sequence encoding SDR, C-14 hydroxylase, C-25 hydroxylase, C-22 hydroxylase, C-2 hydroxylase and C-20 hydroxylase proteins and a suitable signal for regulating transcription/translation can be constructed by a method which is well known to a person in the art. Examples of such method include an in vitro recombination DNA technique, a DNA synthesis technique, and an in vivo recombination technique. The DNA sequence may be effectively linked to a suitable promoter in the expression vector in order to induce synthesis of mRNA. Furthermore, the expression vector may contain, as a site for translation initiation, a ribosome binding site and a transcription terminator.

A preferred example of the recombinant vector of the present invention is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid DNA sequence to protoplasts that can produce a new plant by appropriately inserting a plant cell or hybrid DNA to a genome of a plant. Especially preferred form of Ti-plasmid vector is a so-called binary vector which has been disclosed in EP 0 120 516 B1 and U.S. Pat. No. 4,940,838. Other vector that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be advantageous especially when a plant host cannot be easily transformed.

The expression vector may preferably contain one or more selective marker. Said selective marker is a nucleotide sequence having a property of allowing vector selection by a common chemical method. Every gene that can be used for identifying transformed cells from non-transformed cell can be a selective marker. Examples thereof include a gene resistant to herbicide such as glyphosate and phosphinothricin, and a gene resistant to antibiotics such as kanamycin, G418, bleomycin, hygromycin, and chloramphenicol, but it is not limited thereto.

For the recombinant vector of the present invention, the promoter can be any one of CaMV 35S, actin, ubiquitin, pEMU, MAS or histone promoter, but not limited thereto. The term "promoter" means a DNA molecule to which RNA polymerase binds in order to initiate its transcription, and it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, a constitutive promoter can be preferable for the present invention. Therefore, a possibility for choosing a constitutive promoter is not limited herein.

For the recombinant vector of the present invention, any conventional terminator can be used. Examples thereof include nopaline synthase (NOS), rice α-amylase RAmy 1 A terminator, phaseolin terminator, and a terminator for optopine gene of *Agrobacterium tumefaciens*, etc., but are not limited thereto. Regarding the necessity of terminator, it is generally known that such region can increase a reliability and an efficiency of transcription in plant cells. Therefore, the use of terminator is highly preferable in view of the contexts of the present invention.

Plant transformation means any method by which DNA is delivered to a plant. Such transformation method does not necessarily need a period for regeneration and/or tissue culture. Transformation of plant species is now quite common not only for dicot plants but also for monocot plants. In principle, any transformation method can be used for introducing a hybrid DNA of the present invention to appropriate progenitor cells. The method can be appropriately selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a (DNA or RNA-coated) particle bombardment method for various plant components (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc.

The method for producing a transgenic plant having increased content of 20-hydroxyecdysone of the present invention includes transforming a plant cell with the recombinant vector of the present invention, and the transformation may be mediated by *Agrobacterium* tumefiaciens, for example. Further, the method of the present invention includes regenerating a transgenic plant from the transformed plant cell. As for the method for regenerating a transgenic plant from a transformed plant cell, a method well known in the pertinent art can be used.

The transformed plant cell needs to be regenerated into a whole plant. Techniques for regeneration into a mature plant by culture of callus or protoplast are well known in the pertinent art for various species.

The present invention further provides a transgenic plant produced by the above method which has increased content of 20-hydroxyecdysone compared to a wild type plant, and a seed thereof.

According to one embodiment of the present invention, the plant can be a dicot plant such as tobacco, *Arabidopsis thaliana*, potato, eggplant, pepper, tomato, burdock, crown daisy, lettuce, balloon flower, spinach, chard, yam, celery, carrot, water parsley, parsley, Chinese cabbage, cabbage, *Raphanus sativus* for. raphnistroides MAK, watermelon, oriental melon, cucumber, zucchini, gourd, strawberry, soybean, mung bean, kidney bean, or sweet pea or a monocot plant such as rice, barley, wheat, rye, maze, sugar cane, oat, or onion. Preferably, it is a dicot plant. More preferably, it is tobacco, but it is not limited thereto.

The present invention further provides a composition for increasing content of 20-hydroxyecdysone in plant which includes, as an effective component, one or more genes of insect-derived SDR gene which consists of the nucleotide sequence of SEQ ID NO: 1 or SEQ ID NO: 7 and C-14 hydroxylase gene which consists of the nucleotide sequence of SEQ ID NO: 2 or SEQ ID NO: 8; C-25 hydroxylase gene which consists of the nucleotide sequence of SEQ ID NO: 3 or SEQ ID NO: 9; C-22 hydroxylase gene which consists of the nucleotide sequence of SEQ ID NO: 4 or SEQ ID NO: 10; C-2 hydroxylase gene which consists of the nucleotide sequence of SEQ ID NO: 5 or SEQ ID NO: 11; and C-20 hydroxylase gene which consists of the nucleotide sequence of SEQ ID NO: 6 or SEQ ID NO: 12. As one or more genes of insect-derived SDR gene and C-14 hydroxylase gene; C-25 hydroxylase gene; C-22 hydroxylase gene; C-2 hydroxylase gene; and C-20 hydroxylase gene are contained as an effective component in the composition of the present invention and those genes are used for transformation of a plant, it becomes possible to increase the content of 20-hydroxyecdysone in plant.

The present invention further provides a method for increasing content of 20-hydroxyecdysone in plant including transforming a plant cell with a recombinant vector containing one or more genes encoding one or more proteins of SDR (short-chain dehydrogenase/reductase) protein and C-14 hydroxylase protein; a gene encoding C-25 hydroxylase protein; a gene encoding C-22 hydroxylase protein; a gene encoding C-2 hydroxylase protein; and a gene encoding C-20 hydroxylase protein derived from insect to overexpress the genes.

The scope of the nucleotide sequence of the present invention which encodes SDR, C-14 hydroxylase, C-25 hydroxylase, C-22 hydroxylase, C-2 hydroxylase, and C-20 hydroxylase proteins is as described in the above.

The present invention further provides a method for producing a transgenic plant having increased insect resistance compared to a wild type plant including:

transforming a plant cell with a recombinant vector containing one or more genes encoding one or more proteins of SDR (short-chain dehydrogenase/reductase) protein and C-14 hydroxylase protein; a gene encoding C-25 hydroxylase protein; a gene encoding C-22 hydroxylase protein; a gene encoding C-2 hydroxylase protein; and a gene encoding C-20 hydroxylase protein derived from insect; and regenerating a plant from the transformed plant cell.

As described herein, the expression "insect resistance" includes the resistance and tolerance which is exhibited by a plant against harmful insects, and it includes inhibited preference of harmful insect for host plant, inhibited growth activity of a host against harmful insect, and tolerance not allowing any influence by harmful insects based on strong compensation property or recovery property.

The plant transformed with the recombinant vector of the present invention, which contains a gene encoding one or more proteins of insect-derived SDR protein and C-14 hydroxylase protein; C-25 hydroxylase protein; C-22 hydroxylase protein; C-2 hydroxylase protein; and C-20 hydroxylase protein, has increased content of 20-hydroxyecdysone. Since 20-hydroxyecdysone is known to exhibit an antifeedant effect, avoidance, and insecticidal activity against some harmful insects, the plant transformed with the recombinant vector of the present invention may exhibit enhanced insect resistance due to the influence exhibited by increased 20-hydroxyecdysone.

The present invention further provides a transgenic plant produced by the aforementioned method which has increased insect resistance compared to a wild type plant, and a transgenic seed of the plant.

The plant of the present invention is as described in the above.

The present invention further provides a composition for enhancing insect resistance of a plant which includes, as an effective component, one or more genes of SDR (short-chain dehydrogenase/reductase) gene which consists of the nucleotide sequence of SEQ ID NO: 1 or SEQ ID NO: 7 and C-14 hydroxylase gene which consists of the nucleotide sequence of SEQ ID NO: 2 or SEQ ID NO: 8; C-25 hydroxylase gene which consists of the nucleotide sequence of SEQ ID NO: 3 or SEQ ID NO: 9; C-22 hydroxylase gene which consists of the nucleotide sequence of SEQ ID NO: 4 or SEQ ID NO: 10; C-2 hydroxylase gene which consists of the nucleotide sequence of SEQ ID NO: 5 or SEQ ID NO: 11; and C-20 hydroxylase gene which consists of the nucleotide sequence of SEQ ID NO: 6 or SEQ ID NO: 12.

Hereinbelow, the present invention is explained in greater detail in view of the Examples. However, it is evident that the following Examples are given only for exemplification of the present invention and by no means the present invention is limited to the following Examples.

Examples

Materials and Methods
1. 20-Hydroxyecdysone Biosynthesis Gene from Insect

Figure 2:
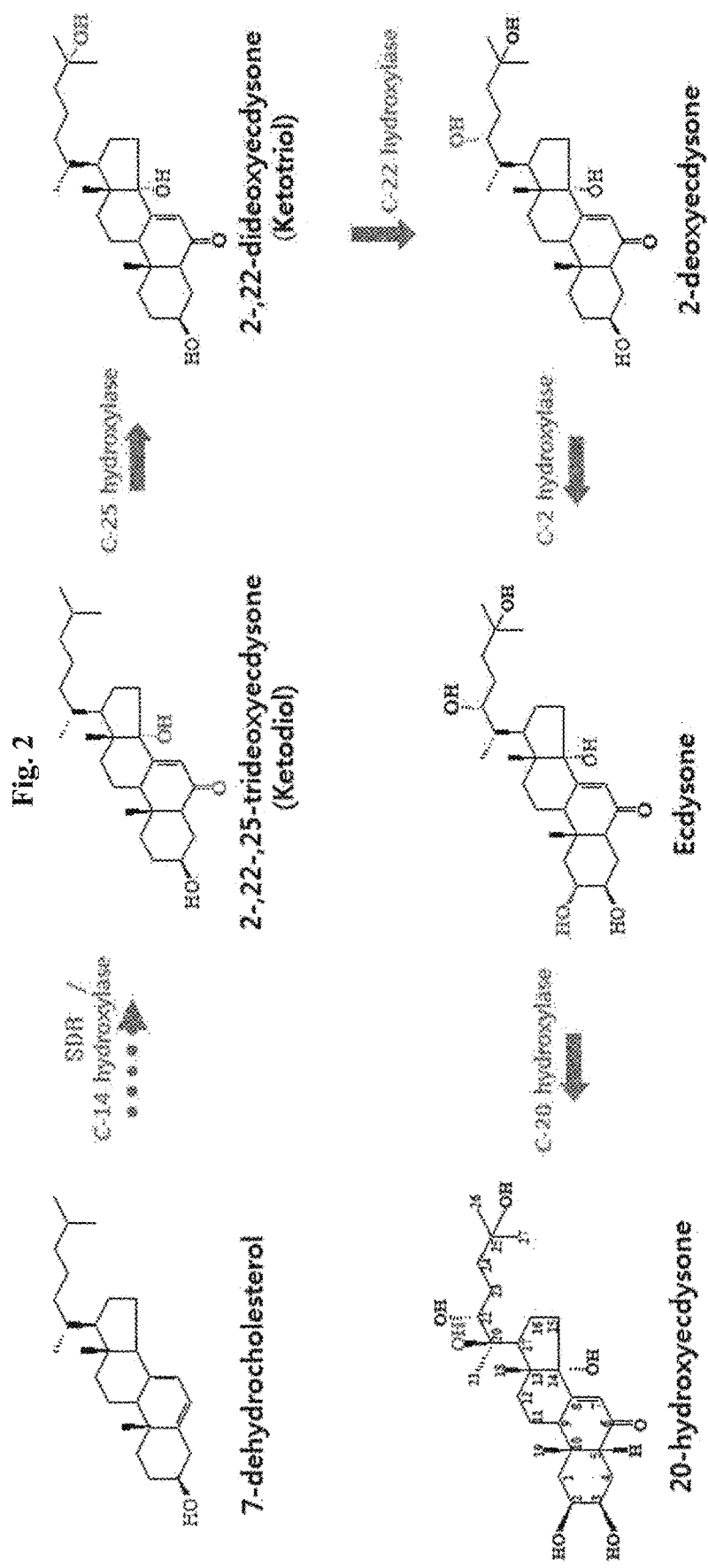
FIG. 2 shows the biosynthetic pathway of 20-hydroxyecdysone (i.e., 20E) in insect, and genes related to the biosynthesis.

For having 20-hydroxyecdysone (hereinbelow, 20E) biosynthesis gene from an insect, information of 6 kinds of gene was collected from *Bombyx mori* (silkworm moth) and *Drosophila melanogaster* (fruit fly) based on the 20E biosynthetic pathway in insect given by KEGG (http://www.kegg.jp/) (FIG. 2). The 6 kinds of gene are SDR (short-chain dehydrogenase/reductase), C-14 hydroxylase, C-25 hydroxylase, C-22 hydroxylase, C-2 hydroxylase, and C-20 hydroxylase, and the 5 kinds except SDR are genes belonging to cytochrome P450 family.

Figure 3:
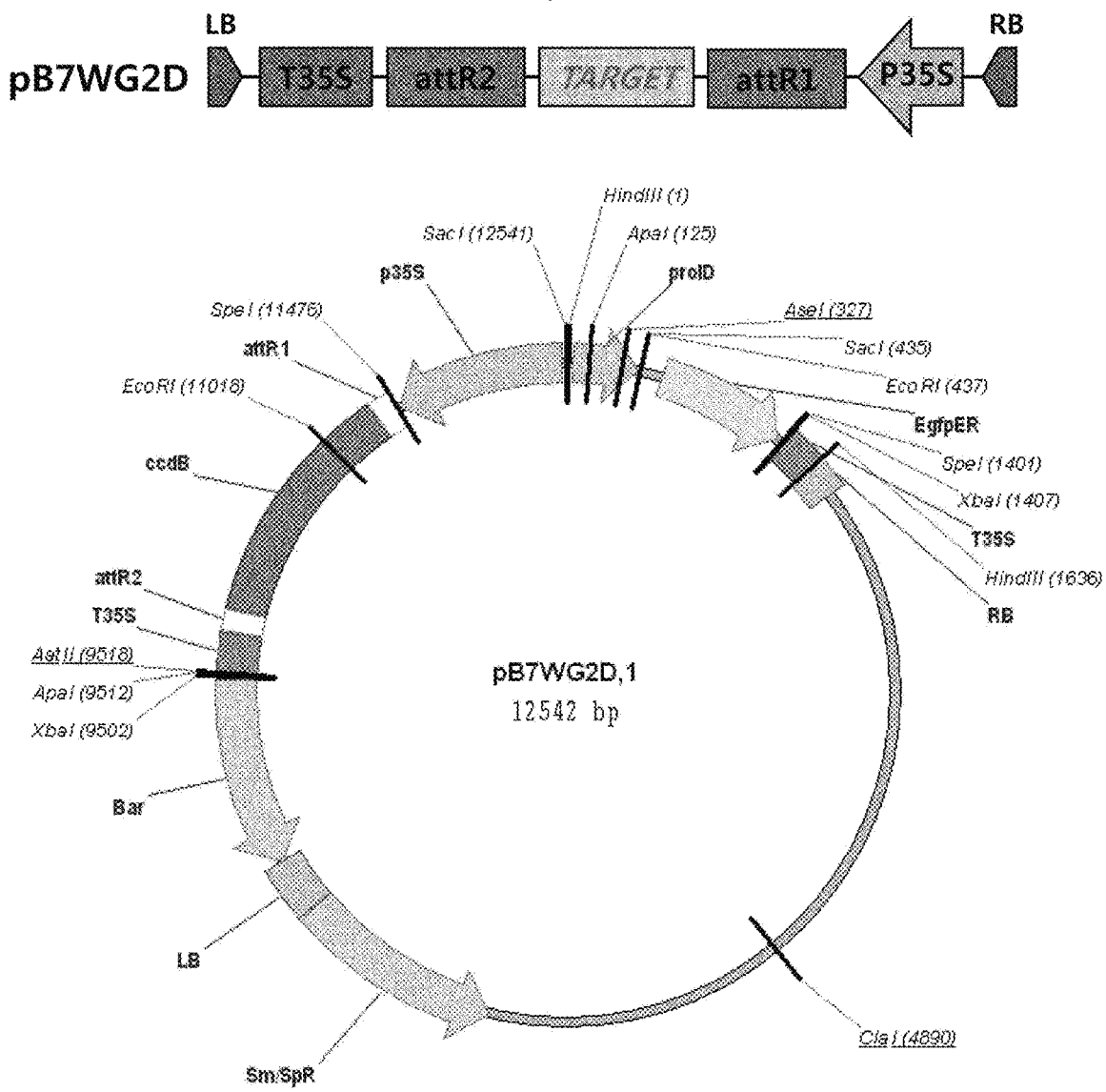
FIG. 3 is a schematic diagram of the recombinant vector containing the insect-derived gene of the present invention.

To have easier expression in plant, the nucleotide sequence of the 6 kinds of gene related to the insect 20E biosynthesis, which are derived from *Bombyx mori* or *Drosophila melanogaster*, were codon-optimized based on the codon usage in maze. The 6 kinds of gene were synthesized based on the codon-optimized nucleotide sequence.
2. Construction of Plant Expression Vector and *Agrobacterium* Transformation Among the 6 kinds of gene synthesized above, each of the 5 kinds derived from *Bombyx mori* (i.e., C-14 hydroxylase, C-25 hydroxylase, C-22 hydroxylase, C-2 hydroxylase and C-20 hydroxylase) and the 6 kinds derived from *Drosophila melanogaster* (SDR, C-14 hydroxylase, C-25 hydroxylase, C-22 hydroxylase, C-2 hydroxylase and C-20 hydroxylase) was inserted to a plant expression vector (pB7WG2D) by using Gateway system. Expression of the each gene was carried out such that it is regulated by 35S promoter, and, as a selection marker, bar, i.e., an herbicide gene, was used (FIG. 3). The constructed plant expression vector was used for transformation of *Agrobacterium tumefaciens* GV2260.
3. Induction of Transient Expression of Insect 20E Biosynthesis Gene in Plant The transformed *Agrobacterium* was inoculated to liquid LB medium (5 mL) containing 100 μg/ml rifampicin and 50 μg/ml spectinomycin, and then subjected to overnight suspension culture at 28° C. under shaking rate of 200 rpm. The suspension culture (1 mL) was inoculated again to liquid LB medium (25 mL) containing 100 μg/ml rifampicin, 50 μg/ml spectinomycin, and 200 μM acetosyringone followed by suspension culture at 28° C. under shaking rate of 200 rpm until $OD_{600}$ is 1.0. After measuring the $OD_{600}$ value, the culture was centrifuged for 10 minutes at 3000 rpm to remove the supernatant. The cell pellet was suspended in 10 mM MES buffer (10 mM $MgCl_2$, 10 mM MES (pH 5.5)). After centrifuging again the suspension for 10 minutes at 3,000 rpm, the supernatant was removed and the cell pellet was re-suspended in 10 mM MES to have final $OD_{600}$ value of 3.0. Then, after adding acetosyringone to final concentration of 200 μM, the mixture was kept overnight at room temperature.

After adding each *Agrobacterium* solution in the same amount, agroinfiltration was carried out. Briefly, it was carried out in a mode in which *Agrobacterium* solution is filled in a 1 ml syringe (without needle) and injected to a backside of the tobacco (*Nicotiana benthamiana*) leaf. Tobacco obtained after agroinfiltration was allowed to grow for 7 days at 27° C., and only the leaf for which the agroinfiltration has been carried out was harvested and used for the analysis.
4. Analysis of Gene Expression and Biosynthesis of 20-Hydroxyecdysone (20E)

Presence or absence of the expression of the gene 20E biosynthesis gene which has been introduced as described in the above was determined by RT-PCR (reverse transcription polymerase chain reaction). RT-PCR was carried out by using, as a template, total RNA (100 ng) extracted from the tobacco leaf after agroinfiltration, and primers for amplifying the introduced 20E biosynthesis gene (Table 1). Conditions of RT-PCR are as follows: 50° C., 30 minutes→95° C., 5 minutes→[95° C., 30 seconds→55° C., 30 seconds→72° C., 1 minute and 30 seconds] (30 cycles)→72° C., 10 minutes.

TABLE 1

RT-PCR Primer Information

| Gene name | | Nucleotide sequence (5' → 3') (SEQ ID NO) |
|---|---|---|
| B. mori C-14 hydroxylase | F | CACCATGAGTTCGCTCATCATTGTG (SEQ ID NO: 13) |
| | R | TCACTTCCGAGGTATCAAATGCATC (SEQ ID NO: 14) |
| B. mori C-25 hydroxylase | F | CACCATGGACCTTTATTTTATTTGGCTG (SEQ ID NO: 15) |
| | R | TCAAATTGGCTCGCAGTAGTACTTC (SEQ ID NO: 16) |

TABLE 1-continued

RT-PCR Primer Information

| Gene name | | Nucleotide sequence (5' → 3') (SEQ ID NO) |
|---|---|---|
| B. mori C-22 hydroxylase | F | CACCATGTTCGTTAGGCTCACCGTT (SEQ ID NO: 17) |
| | R | TCAGGAACTTCTTGGGATGAAGTTG (SEQ ID NO: 18) |
| B. mori C-2 hydroxylase | F | CACCATGCATCGCTTCCCGTCTATGTC (SEQ ID NO: 19) |
| | R | TCACTTAGAAATGCTGCGCGGTAG (SEQ ID NO: 20) |
| B. mori C-20 hydroxylase | F | CACCATGTCTCTCCCGGGAGTTTTCC (SEQ ID NO: 21) |
| | R | TCACCACTCGACAAGACGCAAGG (SEQ ID NO: 22) |
| D. melanogaster SDR | F | CACCATGAGCGGCAGTCAACTTCTC (SEQ ID NO: 23) |
| | R | TCAAATCTTCTCCTGTCTATTCG (SEQ ID NO: 24) |
| D. melanogaster C-14 hydroxylase | F | CACCATGCTGGCTGCTCTGATCTAC (SEQ ID NO: 25) |
| | R | TCATAGTGGTCCGATCTTCTC (SEQ ID NO: 26) |
| D. melanogaster C-25 hydroxylase | F | CACCATGTCAGCGGACATAGTCGA (SEQ ID NO: 27) |
| | R | TCAGTCCTGAACCACAGCTCC (SEQ ID NO: 28) |
| D. melanogaster C-22 hydroxylase | F | CACCATGTTGACCAAGCTGCTAAAG (SEQ ID NO: 29) |
| | R | TCACTCGCGACGGAGGCGCAG (SEQ ID NO: 30) |
| D. melanogaster C-2 hydroxylase | F | CACCATGACCGAGAAGAGGGAGAG (SEQ ID NO: 31) |
| | R | TCACTCTGTCCGTGGCCGGAG (SEQ ID NO: 32) |
| D. melanogaster C-20 hydroxylase | F | CACCATGGCCGTGATACTGTTGCTC (SEQ ID NO: 33) |
| | R | TCAGAAAACGCGATCGCTGAG (SEQ ID NO: 34) |

Furthermore, 20E biosynthesis was determined based on 20E content which is obtained by HPLC (high performance liquid chromatography) analysis. A methanol extract of tobacco leaf after agroinfiltration was prepared for HPLC analysis, and, after removing lipid component by hexane phase partition, it was used for the analysis. Briefly, the harvested tobacco leaf sample was ground, and, to 100 mg of the ground sample, methanol (1 ml) was added and mixed therein. After allowing the mixture to stand for 1 hour at 55° C., it was centrifuged for 10 minutes at 5,000 rpm and only the supernatant was collected. The extraction process was repeated 3 times, and, to the collected methanol extract, distilled water (0.75 ml) and hexane (4 ml) were added to induce phase separation, and then only the methanol supernatant was separated. After drying for 55° C. until the separated methanol layer is completely dry, methanol was added in a specific amount compared to the initial sample amount for dissolution. The solution was then centrifuged for 10 minutes at 12,000 rpm, and then only the supernatant was collected and used for analysis. HPLC Conditions for determination of 20E content are as shown in the following Table 2, and determination of the detected 20E compound was carried out by UPLC-MS/MS (ultra performance liquid chromatography-tandem mass spectrometry), in which UPLC-MS/MS conditions are as shown in the following Table 3.

TABLE 2

HPLC Conditions for determination of 20E content

| Parameter | Conditions |
|---|---|
| Apparatus | Shimadzu HPLC system DGU-20A LC-20AD SIL-20A CTO-20A SPD-M20A CBM-20A |
| Column | Shim-pack GIS ODS column (250 × 4.6 mM ID, 5 μm) |
| Mobile phase | 11% Isopropanol + 0.1% TFA |
| Flow rate | 1 ml/minute |
| Wavelength for detection | 242 nm |
| Wavelength for scanning | 190 to 800 nm |
| Injection amount | 20 μl |
| Column temperature | 40° C. |
| Running time | 60 minutes |

TABLE 3

UPLC-MS/MS Conditions for determination of 20E compound

| Parameter | Conditions |
|---|---|
| Apparatus | UHPLC-MS/MS system Agilent 1290 Infinity UHPLC AB Sciex QTrap 6500 MS/MS |
| Column | SeQuant ZIC-cHILIC (100 × 2.1 mM ID, 3 μm, 100 Å) |
| Mobile phase | A: MeOH (5 mM ammonium acetate, 0.1% formic acid) B: Water (5 mM ammonium acetate, 0.1% formic acid) * A:B = 85:15 |
| Flow rate | 130 μl/minute |
| Injection amount | 5 μl |
| Running time | 5 minutes |

Example 1. Analysis of Expression of Insect-Derived Gene Related to 20E Biosynthesis which has been Introduced to Plant From the tobacco leaf obtained after agroinfiltration by using *Agrobacterium* which has been transduced with a plant expression vector containing each of the 5 kinds of 20E biosynthesis gene derived from *Bombyx mori* (C-14 hydroxylase, C-25 hydroxylase, C-22 hydroxylase, C-2 hydroxylase and C-20 hydroxylase) or 6 kinds of 20E biosynthesis gene derived from *Drosophila melanogaster* (SDR, C-14 hydroxylase, C-25 hydroxylase, C-22 hydroxylase, C-2 hydroxylase and C-20 hydroxylase), presence or absence of the expression of each gene was determined by RT-PCR. As a result, it was found that all of the 5 kinds of gene related to 20E biosynthesis gene are expressed in a tobacco leaf sample in which expression of gene derived from *Bombyx mori* has been induced by agroinfiltration (A of FIG. 4) and also all of the 6 kinds of gene related to 20E biosynthesis gene are expressed in the tobacco leaf sample in which expression of gene derived from *Drosophila melanogaster* has been induced by agroinfiltration (A of FIG. 8).

Figure 4:
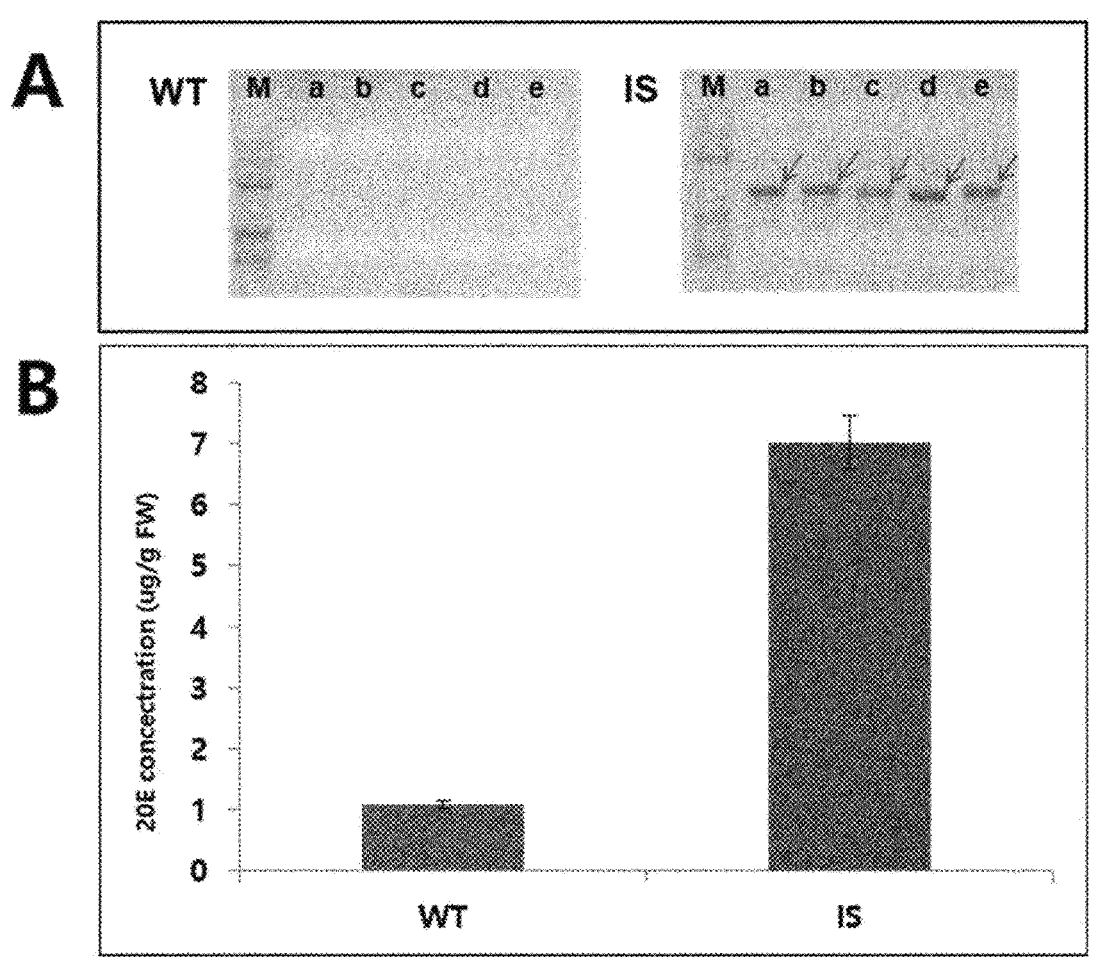
FIG. 4 shows (A) the result of RT-PCR analysis for determining the presence or absence of the expression of 20E biosynthesis gene derived from *Bombyx mori* which has been introduced to a plant, and (B) the result of analysis of 20E content that has been finally produced. In the figure, WT: wild type tobacco, IS: tobacco which has been induced to have expression of 20E biosynthesis gene derived from *Bombyx mori*, M: size marker, a: C-14 hydroxylase, b: C-25 hydroxylase, c: C-22 hydroxylase, d: C-2 hydroxylase, and e: C-20 hydroxylase.
Figure 8:
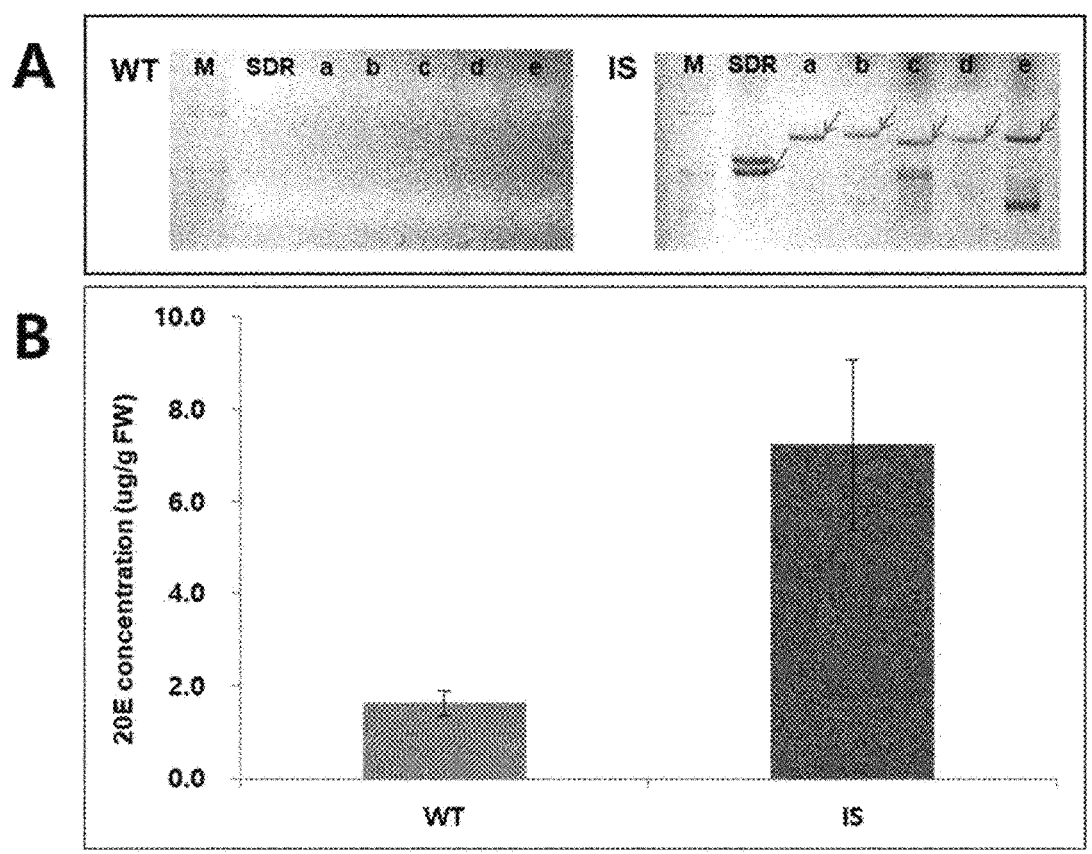
FIG. 8 shows (A) the result of RT-PCR for determining the presence or absence of the expression of 20E biosynthesis gene derived from *Drosophila melanogaster* which has been introduced to a plant, and (B) the result of analyzing 20E content which has been finally produced. In the figure, WT: wild type tobacco, IS: tobacco which has been induced to have expression of 20E biosynthesis gene derived from *Drosophila melanogaster*, M: size marker, SDR: short-chain dehydrogenase/reductase, a: C-14 hydroxylase, b: C-25 hydroxylase, c: C-22 hydroxylase, d: C-2 hydroxylase, and e: C-20 hydroxylase.

Furthermore, as a result of analyzing the 20E content in wild type tobacco leaf and tobacco leaf in which expression of insect-derived gene has been induced, it was found that, compared to the wild type (WT), the 20E content has increased by about 7 times or 4.5 times in the tobacco (IS) in which expression of gene derived from Bombyx mori or Drosophila melanogaster has been induced (B of FIG. 4 and B of FIG. 8).

Example 2. Analysis of Change in 20E Content with or without Addition of 20E Biosynthesis Precursor Derived from Insect As a method for increasing 20E content, a method of adding a precursor is generally known. As such, to the tobacco leaf for which expression of the insect-derived gene related to 20E biosynthesis of the present invention has been introduced, a precursor of biosynthesis of 20E (7-dehydrocholesterol, 7DHC) was added, and a change in 20E content was analyzed accordingly. To a tobacco leaf obtained 2 days after inducing the expression of insect-derived gene, 10 mM MES buffer solution containing 7 DHC at a concentration of 60 ppm was added by infiltration, which has been carried out in the same manner as the agroinfiltration.

Figure 6:
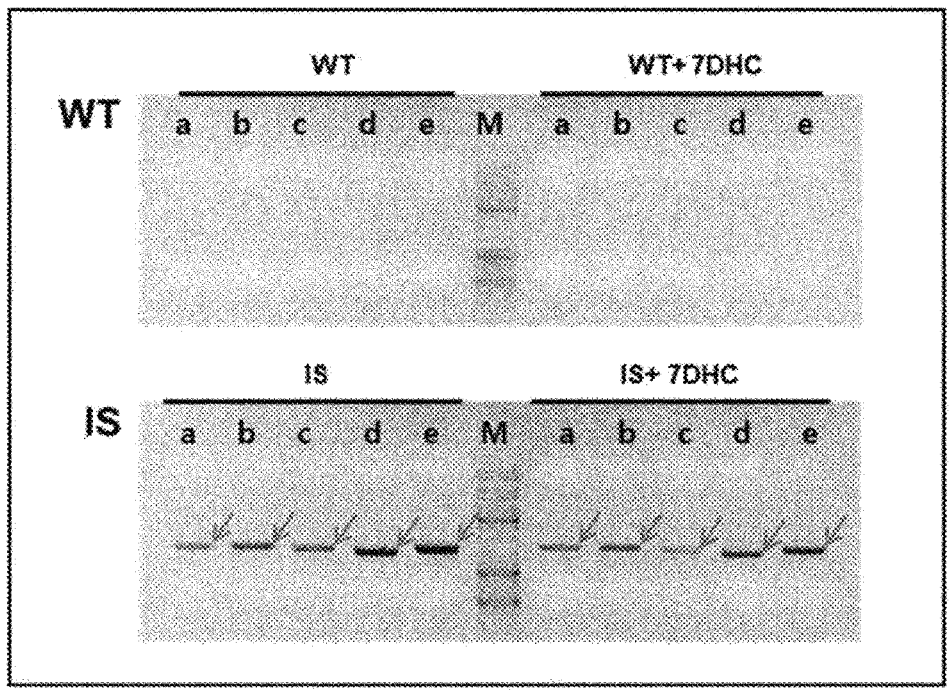
FIG. 6 shows (A) the result of RT-PCR for determining the level of gene expression and (B) the result of analyzing a change in 20E content, both with or without the addition of a precursor of 20E (i.e., 7-dehydrocholesterol, 7DHC) at the time of expression of 20E biosynthesis gene derived from *Bombyx mori* which has been introduced to a plant. In the figure, WT: wild type tobacco, WT+7DHC: wild type tobacco added with a precursor, IS: tobacco which has been induced to have expression of 20E biosynthesis gene derived from *Bombyx mori*, and IS+7DHC: tobacco which has been induced to have expression of 20E biosynthesis gene derived from *Bombyx mori* and added with the precursor.
Figure 6:
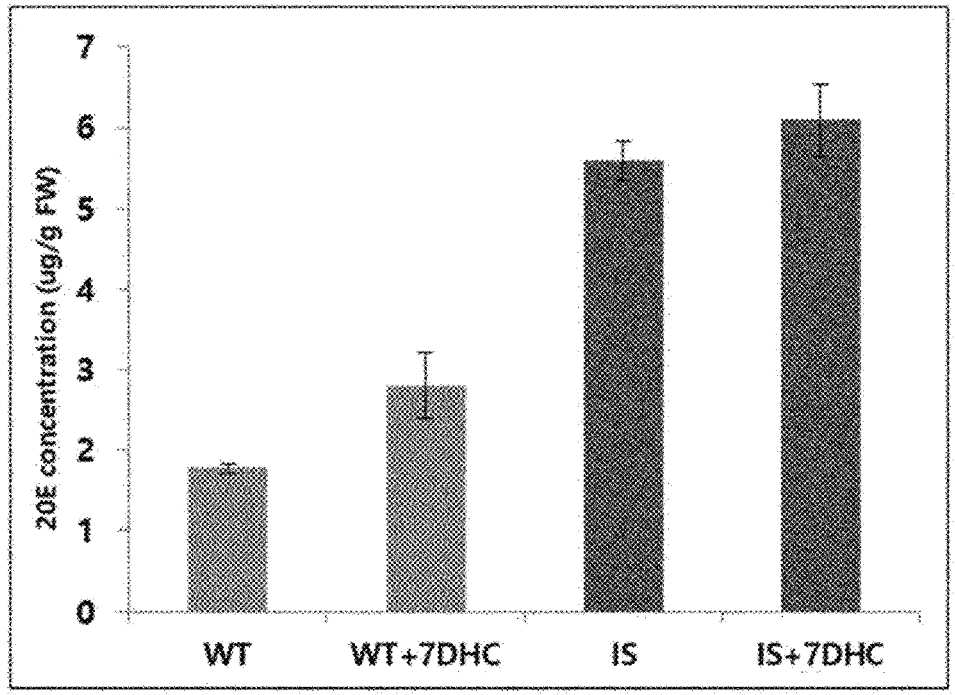
Figure 10:
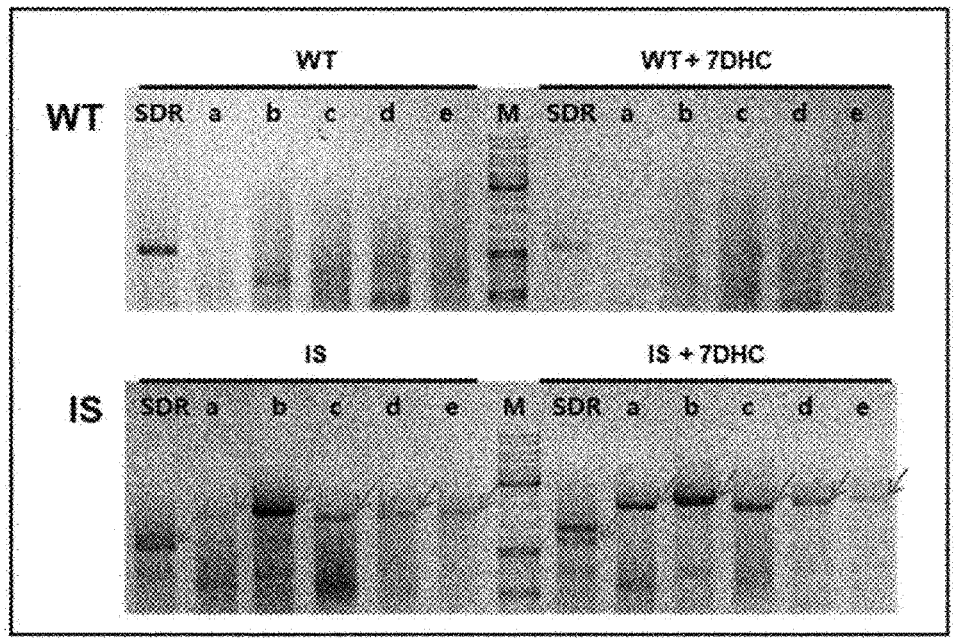
FIG. 10 shows (A) the result of RT-PCR for determining the level of gene expression and (B) the result of analyzing a change in 20E content, both with or without the addition of a precursor of 20E (i.e., 7DHC) at the time of expression of 20E biosynthesis gene derived from *Drosophila melanogaster* which has been introduced to a plant. In the figure, WT: wild type tobacco, WT+7DHC: wild type tobacco added with a precursor, IS: tobacco which has been induced to have expression of 20E biosynthesis gene derived from *Drosophila melanogaster*, and IS+7DHC: tobacco which has been induced to have expression of 20E biosynthesis gene derived from *Drosophila melanogaster* and added with the precursor.
Figure 10:
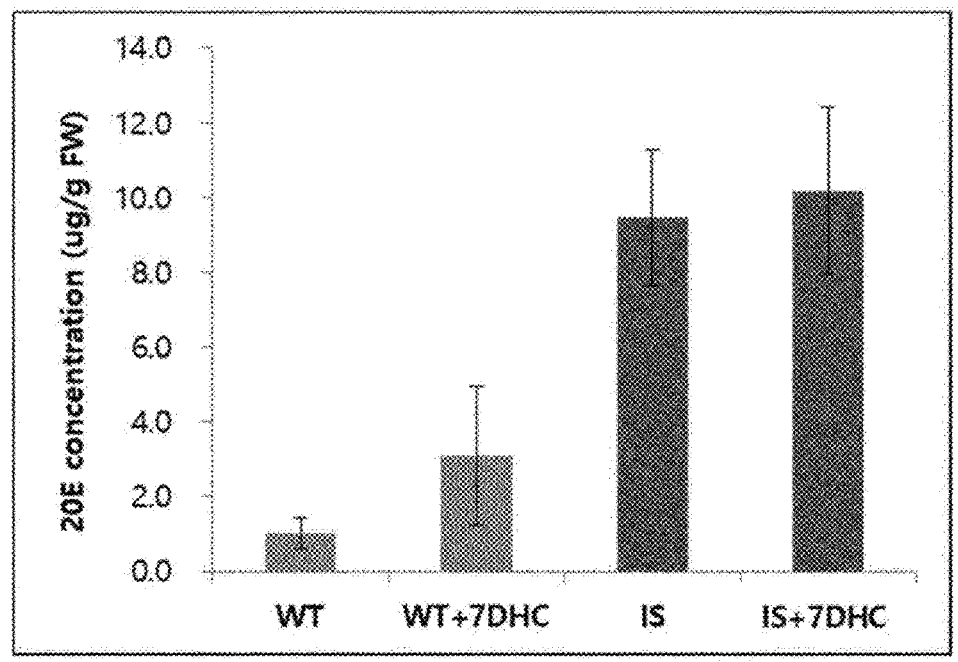

As a result, it was found that, when only the gene related to 20E biosynthesis derived from Bombyx mori or Drosophila melanogaster is expressed (i.e., IS), content of 20E has increased by about 3 times and 9 times, respectively, compared to the wild type (WT). When the precursor 7DHC is added during the expression of the insect-derived gene related to 20E biosynthesis (i.e., IS+7DHC), content of 20E has increased a bit more compared to the case in which the precursor has not been added (i.e., IS) (B of FIG. 6 and B of FIG. 10). These results indicate that the increase in 20E content is caused by the expression of the insect-derived 20E biosynthesis gene.

Example 3. Analysis of Content of 20E and Determination of 20E Compound

Analysis of content of 20E and determination of 20E compound from an extract of tobacco leaf, which has been induced to have expression of 5 kinds or 6 kinds of 20E biosynthesis gene derived from Bombyx mori or Drosophila melanogaster, were carried out by HPLC and UPLC-MS/MS.

Figure 5:
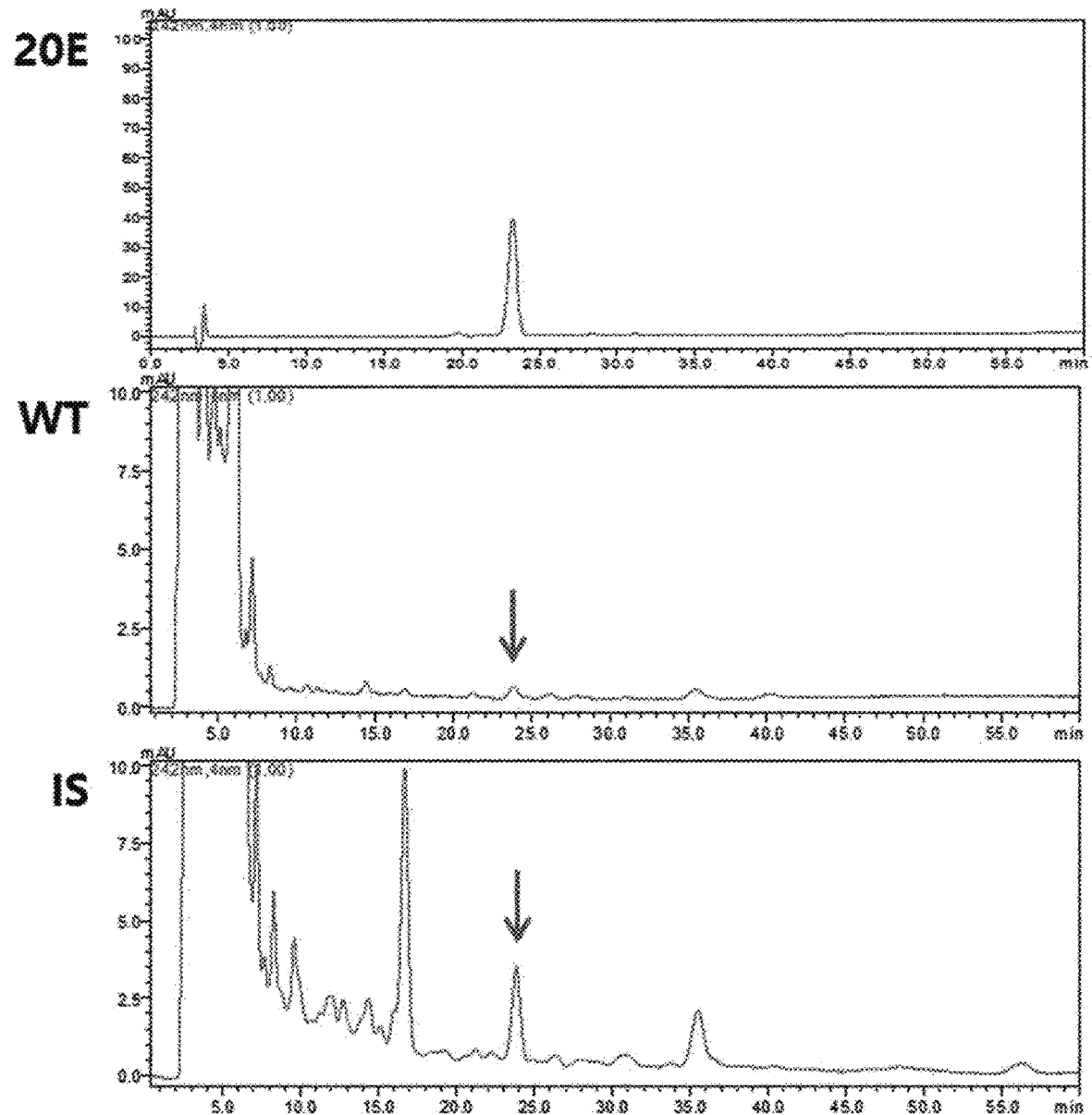
FIG. 5 shows the result of HPLC analysis for determining the 20E content in a plant to which 20E biosynthesis gene derived from *Bombyx mori* has been introduced. In the figure, 20E: standard, WT: wild type tobacco, IS: tobacco which has been induced to have expression of 20E biosynthesis gene derived from *Bombyx mori*.
Figure 7:
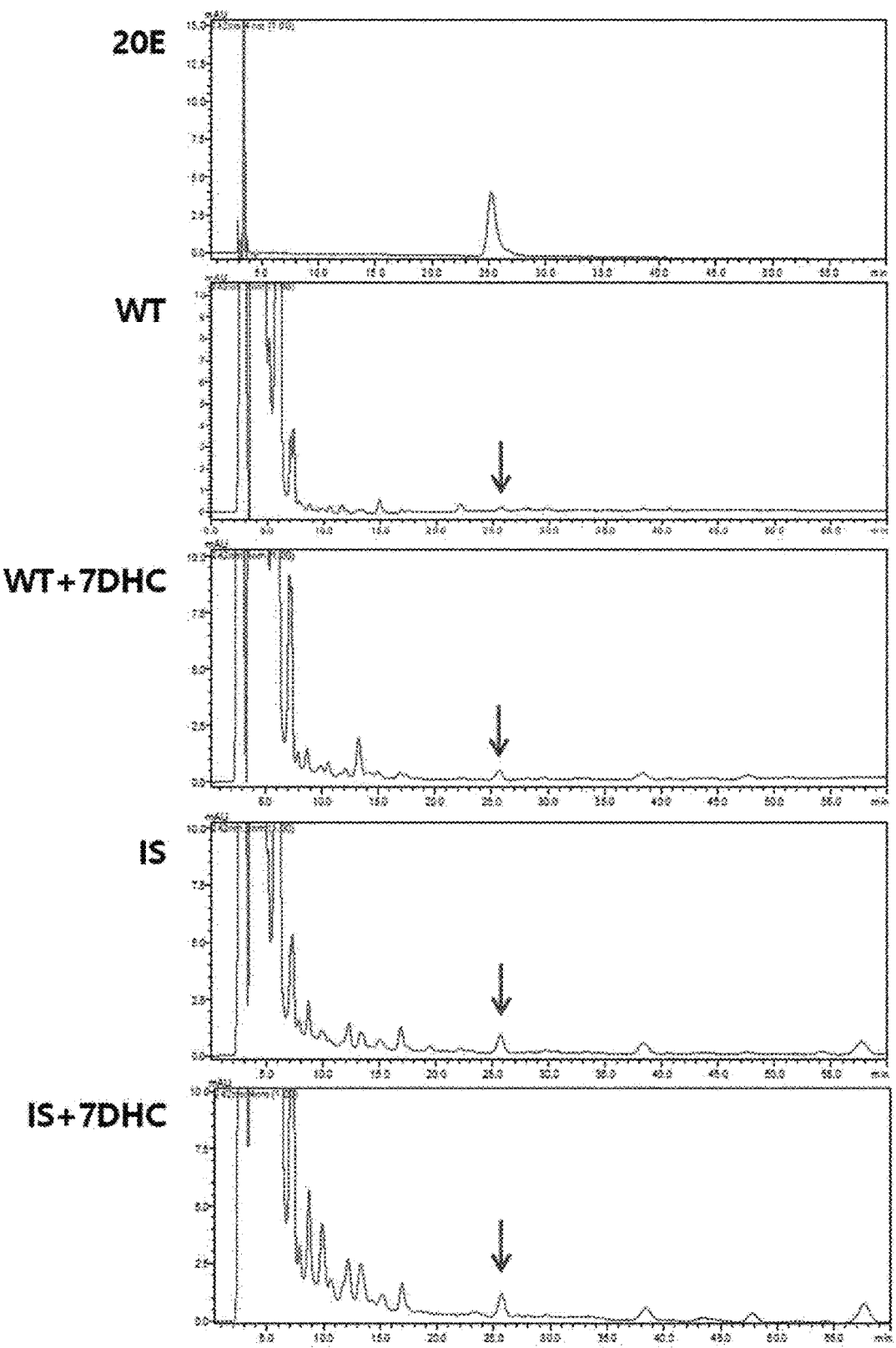
FIG. 7 shows the result of HPLC analysis for determining the 20E content in a plant when 20E precursor (i.e., 7DHC) is added to the plant to which 20E biosynthesis gene derived from *Bombyx mori* has been introduced.
Figure 9:
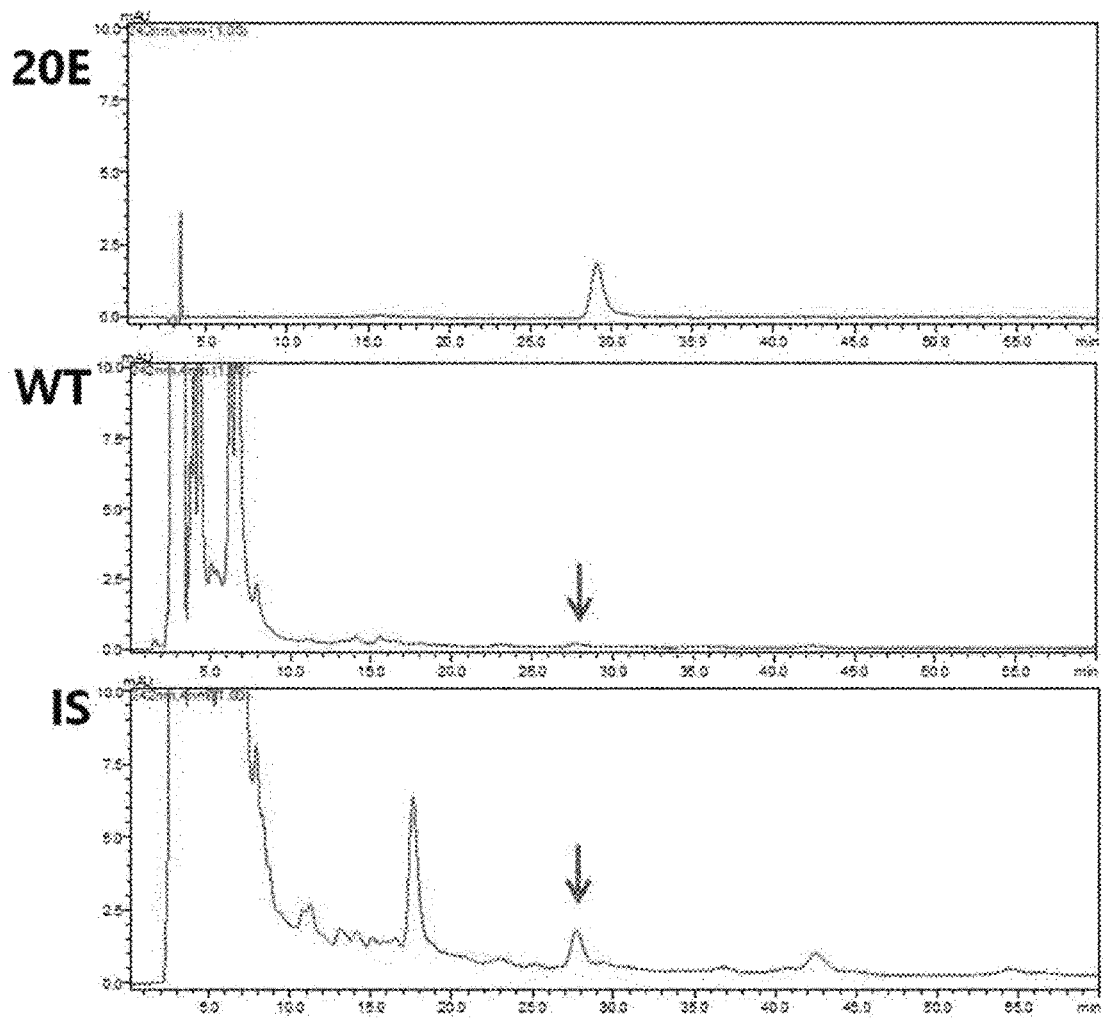
FIG. 9 shows the result of HPLC analysis for determining the 20E content in a plant to which 20E biosynthesis gene derived from *Drosophila melanogaster* has been introduced, in which 20E: standard, WT: wild type tobacco, IS: tobacco which has been induced to have expression of 20E biosynthesis gene derived from *Drosophila melanogaster*.
Figure 11:
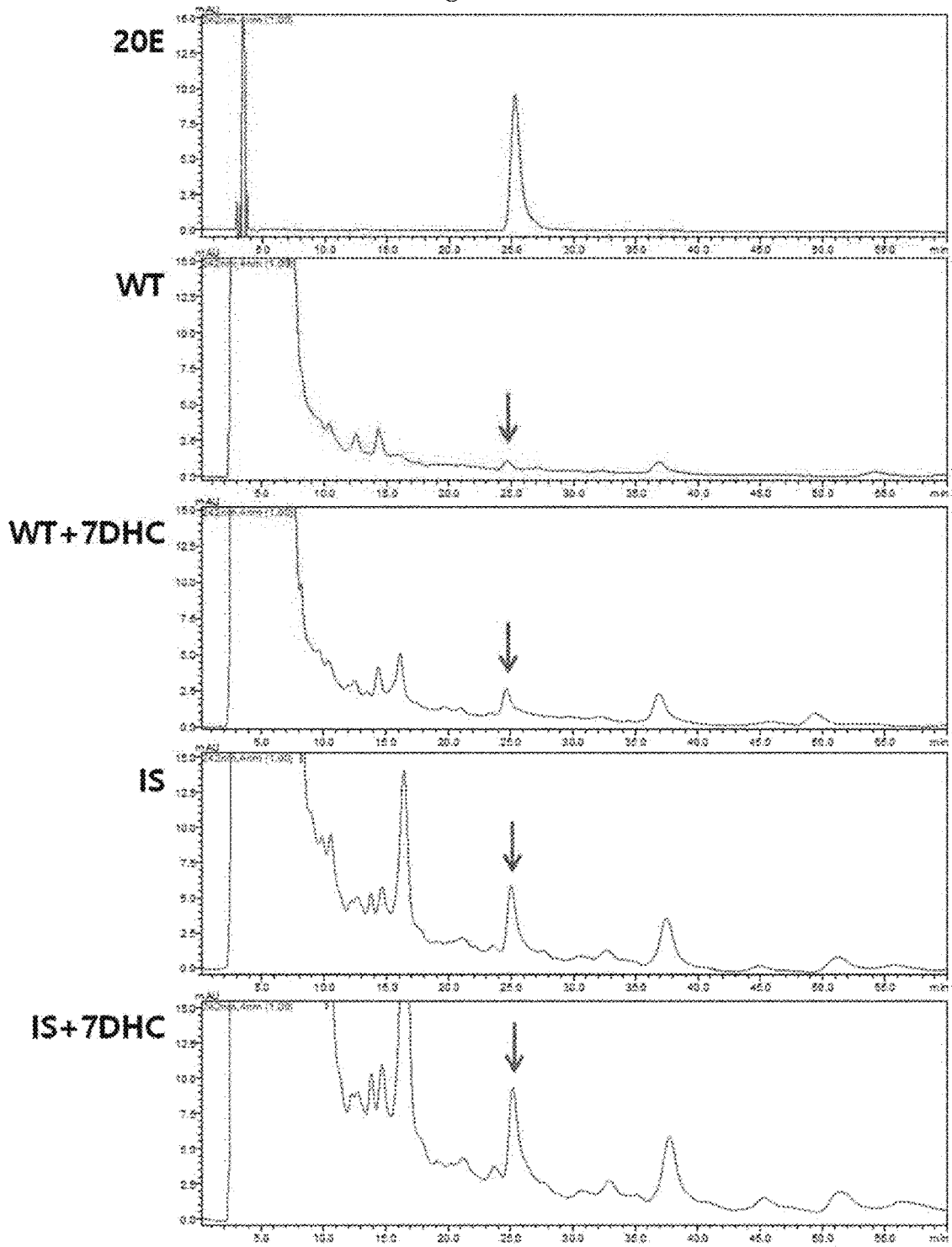
FIG. 11 shows the result of HPLC analysis for determining the 20E content in a plant when 20E precursor (i.e., 7DHC) is added to the plant to which 20E biosynthesis gene derived from *Drosophila melanogaster* has been introduced.

As a result of HPLC, from the tobacco leaf sample induced to have expression of the gene derived from Bombyx mori (FIG. 5 and FIG. 7) or the gene derived from Drosophila melanogaster (FIG. 9 and FIG. 11), a peak was found in the time range that is close to the retention time of 20E standard.

Figure 12:
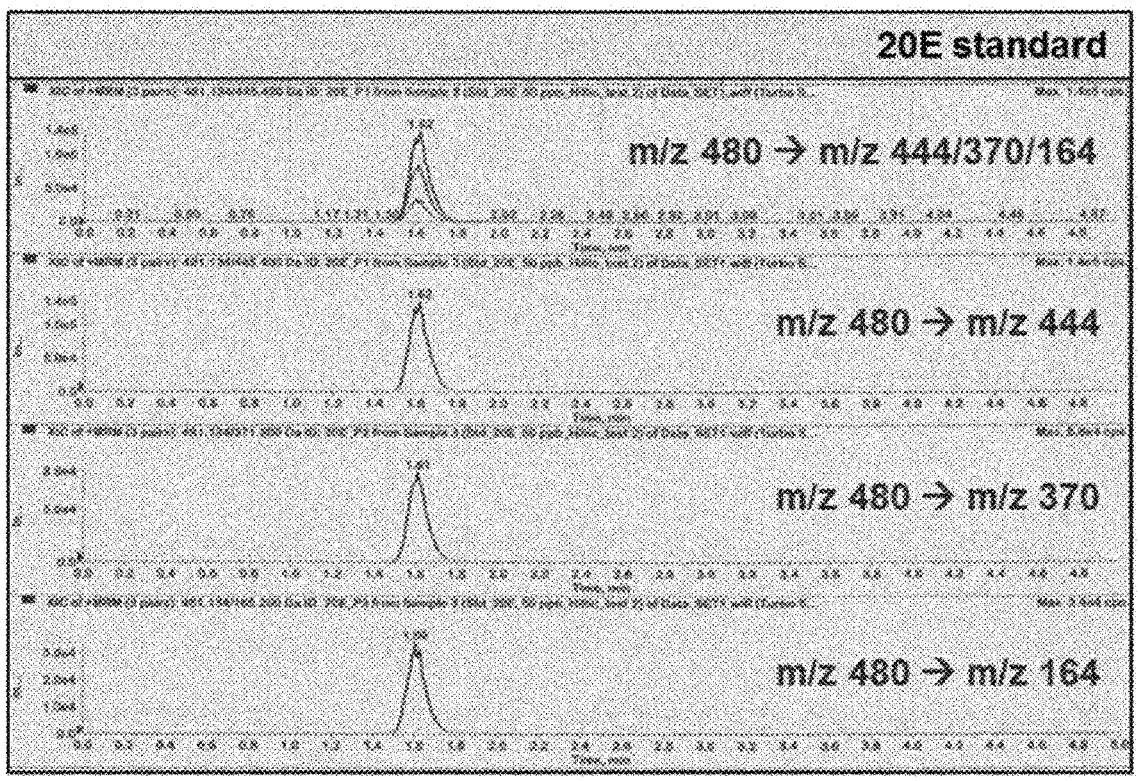
FIG. 12 shows the result of UPLC-MS/MS analysis of the 20E compound as a final product, in which 20E standard: 20-hydroxyecdysone standard, tobacco leaf extract: leaf extract of tobacco which has been induced to have expression of 20E biosynthesis gene derived from insect.
Figure 12:
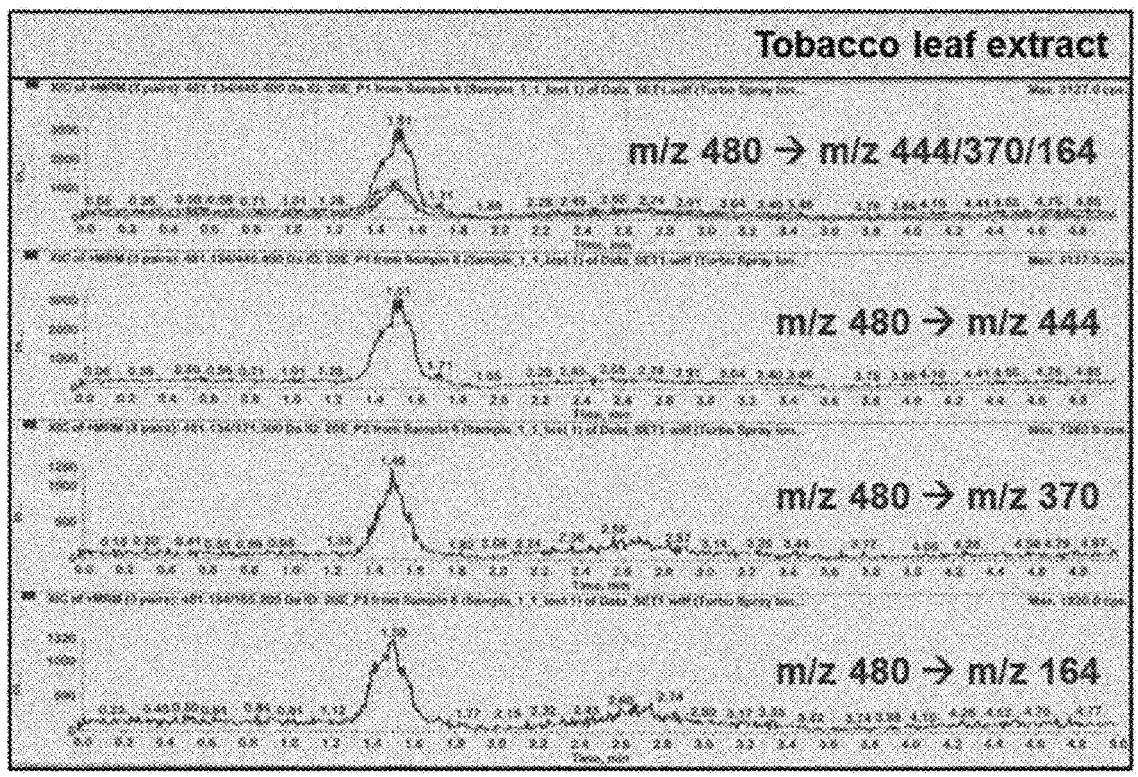

As a result of UPLC-MS/MS, it was found that the molecular weight of 20E standard is 480 Da and fragments with a size of 444, 370, or 164 Da are generated by fragmentation of the molecule, and, since the 20E-like peak of the tobacco extract also exhibits the same fragmentation pattern as the standard, it was recognized as 20E (FIG. 12).

A sequence listing electronically submitted with the present application on Apr. 27, 2020 as an ASCII text file named 20200427_Q30120GR06_TU_SEQ, created on Apr. 23, 2020 and having a size of 29,000 bytes, is incorporated herein by reference in its entirety.

What is claimed is:

1. A method for producing a transgenic plant having increased content of 20-hydroxyecdysone compared to a wild type plant, the method comprising:
   transforming a plant cell with a recombinant vector comprising:
      at least one of a coding sequence encoding a short-chain dehydrogenase/reductase (SDR) protein and a coding sequence encoding a C-14 hydroxylase protein;
      a coding sequence encoding a C-25 hydroxylase protein;
      a coding sequence encoding a C-22 hydroxylase protein;
      a coding sequence encoding a C-2 hydroxylase protein; and
      a coding sequence encoding a C-20 hydroxylase protein derived from insect; and
   regenerating a plant from the transformed plant cell,
   wherein the coding sequence encoding the SDR protein consists of the nucleotide sequence of SEQ ID NO: 1 or SEQ ID NO: 7;
   the coding sequence encoding the C-14 hydroxylase protein consists of the nucleotide sequence of SEQ ID NO: 2 or SEQ ID NO: 8;
   the coding sequence encoding the C-25 hydroxylase protein consists of the nucleotide sequence of SEQ ID NO: 3 or SEQ ID NO: 9;
   the coding sequence encoding the C-22 hydroxylase protein consists of the nucleotide sequence of SEQ ID NO: 4;
   the coding sequence encoding the C-2 hydroxylase protein consists of the nucleotide sequence of SEQ ID NO: 5 or SEQ ID NO: 11; and
   the coding sequence encoding the C-20 hydroxylase protein consists of the nucleotide sequence of SEQ ID NO: 6.

2. A transgenic plant produced by the method of claim 1, the transgenic plant having increased content of 20-hydroxyecdysone compared to the wild type plant.

3. A transgenic seed of the transgenic plant according to claim 2.

4. A composition for increasing content of 20-hydroxyecdysone in plant, the composition comprising:
   at least one of a short-chain dehydrogenase/reductase (SDR) coding sequence which consists of the nucleotide sequence of SEQ ID NO: 1 or SEQ ID NO: 7 and a C-14 hydroxylase coding sequence which consists of the nucleotide sequence of SEQ ID NO: 2 or SEQ ID NO: 8;
   a C-25 hydroxylase coding sequence which consists of the nucleotide sequence of SEQ ID NO: 3 or SEQ ID NO: 9;
   a C-22 hydroxylase coding sequence which consists of the nucleotide sequence of SEQ ID NO: 4;
   a C-2 hydroxylase coding sequence which consists of the nucleotide sequence of SEQ ID NO: 5 or SEQ ID NO: 11; and
   a C-20 hydroxylase coding sequence which consists of the nucleotide sequence of SEQ ID NO: 6.

5. A method for producing a transgenic plant having increased insect resistance compared to a wild type plant, the method comprising:
   transforming a plant cell with a recombinant vector comprising:
      at least one of a coding sequence encoding a short-chain dehydrogenase/reductase (SDR) protein and a coding sequence encoding a C-14 hydroxylase protein;
      a coding sequence encoding a C-25 hydroxylase protein;
      a coding sequence encoding a C-22 hydroxylase protein;
      a coding sequence encoding a C-2 hydroxylase protein; and
      a coding sequence encoding a C-20 hydroxylase protein derived from an insect; and
   regenerating a plant from the transformed plant cell,
   wherein the coding sequence encoding the SDR protein consists of the nucleotide sequence of SEQ ID NO: 1 or SEQ ID NO: 7;
   the coding sequence encoding the C-14 hydroxylase protein consists of the nucleotide sequence of SEQ ID NO: 2 or SEQ ID NO: 8;
   the coding sequence encoding the C-25 hydroxylase protein consists of the nucleotide sequence of SEQ ID NO: 3 or SEQ ID NO: 9;
   the coding sequence encoding the C-22 hydroxylase protein consists of the nucleotide sequence of SEQ ID NO: 4;
   the coding sequence encoding the C-2 hydroxylase protein consists of the nucleotide sequence of SEQ ID NO: 5 or SEQ ID NO: 11; and
   the coding sequence encoding the C-20 hydroxylase protein consists of the nucleotide sequence of SEQ ID NO: 6.

6. A transgenic plant produced by the method of claim 5, the transgenic plant having increased insect resistance compared to the wild type plant.

7. A transgenic seed of the transgenic plant according to claim 6.

8. The method of claim 1, wherein the vector comprises the coding sequence encoding the short-chain dehydrogenase/reductase (SDR) protein.

9. The method of claim 1, wherein the vector comprises the coding sequence encoding the C-14 hydroxylase protein.

10. The method of claim 1, wherein the vector comprises both the coding sequence encoding the short-chain dehydrogenase/reductase (SDR) protein and the coding sequence encoding the C-14 hydroxylase protein.

11. The method of claim 9, wherein the coding sequence encoding the C-14 hydroxylase protein consists of the nucleotide sequence of SEQ ID NO: 2;
    the coding sequence encoding the C-25 hydroxylase protein consists of the nucleotide sequence of SEQ ID NO: 3;
    the coding sequence encoding the C-22 hydroxylase protein consists of the nucleotide sequence of SEQ ID NO: 4;
    the coding sequence encoding the C-2 hydroxylase protein consists of the nucleotide sequence of SEQ ID NO: 5; and
    the coding sequence encoding the C-20 hydroxylase protein consists of the nucleotide sequence of SEQ ID NO: 6.

12. The method of claim 1, wherein the plant is selected from the group consisting of tobacco, *Arabidopsis thaliana*, potato, eggplant, pepper, tomato, burdock, crown daisy, lettuce, balloon flower, spinach, chard, yam, celery, carrot, water parsley, parsley, Chinese cabbage, cabbage, *Raphanus sativus* for. raphnistroides MAK, watermelon, oriental melon, cucumber, zucchini, gourd, strawberry, soybean, mung bean, kidney bean, sweet pea, rice, barley, wheat, rye, maze, sugar cane, oat, and onion.

13. The method of claim 1, wherein the plant is tobacco.

14. A recombinant vector comprising the composition of claim 4.

* * * * *